United States Patent
Paradis et al.

(10) Patent No.: US 10,555,870 B2
(45) Date of Patent: *Feb. 11, 2020

(54) NON-INVASIVE DEVICE FOR SYNCHRONIZING CHEST COMPRESSION AND VENTILATION PARAMETERS TO RESIDUAL MYOCARDIAL ACTIVITY DURING CARDIOPULMONARY RESUSCITATION

(71) Applicant: ZOLL Medical Corporation, Chelmsford, MA (US)

(72) Inventors: Norman Paradis, Putney, VT (US); David Barash, Concord, MA (US); Henry R. Halperin, Baltimore, MD (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 287 days.

This patent is subject to a terminal disclaimer.

(21) Appl. No.: 15/791,937

(22) Filed: Oct. 24, 2017

(65) Prior Publication Data
US 2018/0133105 A1 May 17, 2018

Related U.S. Application Data

(60) Continuation of application No. 15/040,682, filed on Feb. 10, 2016, now Pat. No. 9,833,378, which is a
(Continued)

(51) Int. Cl.
*A61H 31/00* (2006.01)
*A61N 1/39* (2006.01)
(Continued)

(52) U.S. Cl.
CPC ......... *A61H 31/006* (2013.01); *A61H 9/0078* (2013.01); *A61H 31/005* (2013.01);
(Continued)

(58) Field of Classification Search
CPC .. A61H 31/006; A61H 9/0078; A61H 31/005; A61H 2201/5007;
(Continued)

(56) References Cited

U.S. PATENT DOCUMENTS 4,198,963 A 4/1980 Barkalow et al.
4,273,114 A 6/1981 Barkalow et al.
(Continued)

OTHER PUBLICATIONS

Asthon et al., "Effect of rescuer fatigue on performance of continuous external chest compressions over 3 min", Resuscitation, Nov. 2002;55(2):151-5.
(Continued)

*Primary Examiner* — Carl H Layno
*Assistant Examiner* — Erin M Piateski
(74) *Attorney, Agent, or Firm* — ZOLL Medical Corporation

(57) ABSTRACT

A system for improving cardiac output of a patient suffering from pulseless electrical activity or shock and yet displays myocardial wall motion including: a sensor to detect myocardial activity to determine the presence of residual left ventricular pump function having a contraction or ejection phase and a filling or relaxation phase, a device to prompt the application of or apply a compressive force repeatedly applied to the chest based on the sensed myocardial activity such that the compressive force is applied during at least some of the ejection phases and is ceased during at least some of the relaxation phases to permit residual cardiac filling, thereby enhancing cardiac output and organ perfusion.

21 Claims, 11 Drawing Sheets

Related U.S. Application Data division of application No. 13/182,800, filed on Jul. 14, 2011, now Pat. No. 9,259,543, which is a continuation-in-part of application No. 12/685,289, filed on Jan. 11, 2010, now Pat. No. 8,870,797, which is a division of application No. 10/973,775, filed on Oct. 25, 2004, now Pat. No. 7,645,247.

(60) Provisional application No. 61/419,525, filed on Dec. 3, 2010.

(51) Int. Cl.
*A61H 9/00* (2006.01)
*A61M 16/00* (2006.01)

(52) U.S. Cl.
CPC .... *A61N 1/3987* (2013.01); *A61H 2201/5007* (2013.01); *A61H 2201/5097* (2013.01); *A61H 2230/045* (2013.01); *A61H 2230/045* (2013.01); *A61M 16/0057* (2013.01); *A61M 16/0063* (2014.02); *A61M 2205/33* (2013.01); *A61M 2205/332* (2013.01); *A61M 2205/581* (2013.01); *A61M 2205/583* (2013.01); *A61M 2230/04* (2013.01); *A61M 2230/202* (2013.01); *A61M 2230/30* (2013.01)

(58) Field of Classification Search
CPC ........ A61H 2201/5097; A61H 2230/00; A61H 2230/045; A61N 1/3987; A61M 16/0063; A61M 16/0057; A61M 2205/33; A61M 2205/332; A61M 2205/581; A61M 2205/583; A61M 2230/04; A61M 2230/202; A61M 2230/30
USPC .......................................................... 600/16
See application file for complete search history.

(56) References Cited

U.S. PATENT DOCUMENTS

| | | | |
|---|---|---|---|
| 4,928,674 A | 5/1990 | Halperin et al. | |
| 5,020,516 A | 6/1991 | Biondi et al. | |
| 5,490,820 A | 2/1996 | Schock et al. | |
| 5,496,257 A | 3/1996 | Kelly | |
| 5,496,351 A | 3/1996 | Plicchi et al. | |
| 6,053,869 A | 4/2000 | Kawagishi et al. | |
| 6,234,985 B1 | 5/2001 | Lurie et al. | |
| 6,298,267 B1 | 10/2001 | Rosborough et al. | |
| 6,351,671 B1 | 2/2002 | Myklebust et al. | |
| 6,480,733 B1 | 11/2002 | Turcott | |
| 6,620,116 B2 | 9/2003 | Lewis | |
| 6,752,771 B2 | 6/2004 | Rothman et al. | |
| 7,220,235 B2 | 5/2007 | Geheb et al. | |
| 7,645,247 B2 | 1/2010 | Paradis | |
| 9,259,543 B2* | 2/2016 | Paradis | A61H 9/0078 |
| 9,833,378 B2* | 12/2017 | Paradis | A61H 9/0078 |
| 2001/0027279 A1 | 10/2001 | Rothman et al. | |
| 2004/0039313 A1 | 2/2004 | Sherman et al. | |
| 2004/0162587 A1* | 8/2004 | Hampton | A61H 31/005 607/5 |
| 2004/0215244 A1* | 10/2004 | Marcovecchio | A61N 1/39 607/5 |
| 2004/0230140 A1* | 11/2004 | Steen | A61H 31/008 601/41 |
| 2005/0080363 A1 | 4/2005 | Jensen et al. | |
| 2005/0256415 A1 | 11/2005 | Tan et al. | |
| 2006/0089574 A1* | 4/2006 | Paradis | A61H 31/005 601/41 |
| 2006/0100556 A1 | 5/2006 | Hargens et al. | |
| 2006/0190045 A1 | 8/2006 | Marcus et al. | |
| 2007/0060785 A1 | 3/2007 | Freeman et al. | |
| 2008/0082135 A1 | 4/2008 | Arcot-Krishnamurthy et al. | |
| 2008/0161894 A1 | 7/2008 | Ben-David et al. | |
| 2012/0016179 A1* | 1/2012 | Paradis | A61H 9/0078 600/17 |

OTHER PUBLICATIONS

Bayly et al., "Synchronous versus nonsynchronous high-frequency jet ventilation: effects on cardiorespiratory variables and airway pressures in postoperative patients". Crit Care Med. Oct. 1987; 15(10):915-7.

Bendjelid et al., Correlation between measured inferior vena cava diameter and right atrial pressure depends on the echocardiographic method used in patients who are mechanically ventilated, J Am Soc Echocardiogr, Sep. 2002; 15(9):944-9.

Bocka et al., Electromechanical Dissciation in Human Beings: An Echocardiographic Evaluation, Annals of Emergency Medicine, May 1988, p. 450-452.

Boese et al.. "Optomizlng temporal resolution in CT with retrospective ECG gating", Radiologe. Feb. 2000;40(2): 123-9.

Bottiger et al., Emergency medicine—new concepts and therapies improve outcome from cardiac arrest, Anasthesiol lntensivmed Notfallmed Schmerztyer. Jan. 2003; 38(1}:63-7.

Bradley et al., "Blood flow: magnetic resonance imaging", Radiology. Feb. 1985; 154(2):443-50.

Brindley et al. "Predictors of survival following in-hospital adult cardiopulmonary resuscitation". Division of Critical Care Medicine, University of Alberta, Edmonton. no date.

Brindley, "Predictors of survival following in-hospital adult cardiopulmonary resuscitation" CMAJ •Aug. 20, 2002; 167 (4) (2002).

Cobb et al, "Changing incidence of out-of-hospital ventricular fibrillation, 1980-2000". JAMA. Dec. 18, 2002(288(23):3008-13.

Counselman et al., "The status of bedside ultrasonography training in emergency medicine residency programs", Acad Emerg Med. Jan. 2003;10(1 ):37-42.

Etiology, Electrophysiology, and Myocardial Mechanics of Pulseless Electrical Activity, Ture and Psedo-Pulseless Electrical Activity, p. 331-332, 1989, 1992.

Gebber GL, "Basis for phase relations between baroreceptor and sympathetic nervous discharge", Am J Physiol, Feb. 1976; 230(2): 263-70.

Hayes et al., "Monitoring during cardiac arrest: are we there yet?", Curr Opin Crit Care., Jun. 2003; 9(3): 211-7.

International Search Report dated Mar. 5, 2012.

Lanzer et al., "Cardiac imaging using gated magnetic resonance", Radiology. Jan. 1984; 150(1 )0;121-7.

Lanzer et al., "ECG-synchronized cardiac MR imaging: method and evaluation", Radiology. Jun. 1985; 155(3):;681-6.

Linder et at., "New mechanical methods for cardipulmonary resuscitation (CPR). Literature study and analysis of effectiveness", Anaesthesist, Mar. 1997;46(3):220-30.

Liu et al, "An efficient MR phosphorus spectroscopic localization technique for studying ischemic heart", J Magn Reson Imaging. Nov. 1999; 10(5):892-8.

Lorusso et al., Hemodynamic effects in acute cardiomyoplasty of different wrapped muscle activation times as measured by pressure-volume relation, J Card Surg. May-Jun. 1996;11 (3):217-25.

Marek et al., "Correction of morphology and indicators of atrial function using long-term physiologic cardiac pacing in patients with prior chronic atrioventricular dissociation or WI pacing", Vnltr Lek. Sep. 1999;p. 45(9):513-7.

Modersohn et al., "Diastolic heart function—pathophysiology, characterization, and therapeutic approaches", Clin Cardiol. Dec. 1993; 16(12):850-8.

Morris-Thurgood et al., "Pacing in heart failure: improved ventricular interaction in diastole rather than systolic re-synchronization", Europace, Oct. 2000;2(4):271-5; discussion 276.

Ordonez et al., "Assessment of the effectiveness of descending aortomyop!asty for nonischemic cardiac failure by means of the subendocardial viability index", Ann Thorac Cardiovasc Surg. Feb. 2001;7(1 ):17-22.

(56) References Cited

OTHER PUBLICATIONS

Paradis et al., "Aortic Pressure during Human Cardia Arrest: Identification of Psedo-Electromechanical Dissociation", Chest, Jan. 1992, pp. 123-128.

Parish et al., "Success changes the problem:why ventricular fibrillation is decling, why pulseless electrical activity is emerging, and what to do about it", Resuscitation, Jul. 2003; 58(1): 31.

Rudiger, A et al., "Frequency and outcome of in-hospital resuscitation outside the ICU-setting", Swiss Med Wkly., Jan. 24, 2004: 134(3-4):59-62.

Thornton et al., "Dynamic stiffness and implications for assisting the operation of the left ventricle", IMA J Math Appl Med Bioi. Dec. 1996; 13(4):275-95.

Tortoli et al., Toward a better quantitative Measurement of Aortic Flow, Elsevier, Ultrasound in Med & Biol vol. 28, No. 2, pp. 249-257, 2002.

Veenstra et al., "Electrotonic interactions between aggregates of chick embryo cardiac pacemaker cells", Am J Physiol. Mar. 1986; 250(3 Pt 2):H453-63.

Vinet et al, "Analysis of an iterative difference equation model of the cardiac cell membrane", J Theor Bioi. Sep. 21, 1994; 170(2):201-14.

Vural et al., "Optimization of synchronization delay in latissimus dorsi dynamic cardiomyoplasty", Ann Thorac Surg. May 1998;65(5)1231-4.

Wenzel "Arginine vasopressin during cardiopulmonary resuscitation: Laboratory evidence, clinical experience and recommendations, and a view to the future" Crit Care Med 2002 vol. 30, No. 4 (Suppl.) (2002).

Wenzel, "Arginine vasopressin during cardiopulmonary resuscitation: laboratory evidence, clinical experience and recommendations, and a view to the future", Department of Anesthesiologh and Critical Care Medicine, Leopold•Franzens-University, Innsbruck, Austria.

Wenzel, Drug theraphy in cardiopulmonary resuscitation, Wien K!in Wochenschr, Dec. 17, 2001;113(23-24):915-26.

* cited by examiner

NON-INVASIVE DEVICE FOR SYNCHRONIZING CHEST COMPRESSION AND VENTILATION PARAMETERS TO RESIDUAL MYOCARDIAL ACTIVITY DURING CARDIOPULMONARY RESUSCITATION

RELATED APPLICATIONS

This application is a continuation of U.S. patent application Ser. No. 15/040,682 (U.S. Pat. No. 9,833,378) filed Feb. 10, 2016, which is a divisional of U.S. patent application Ser. No. 13/182,800 (U.S. Pat. No. 9,259,543) filed Jul. 14, 2011, which is a continuation-in-part (CIP) of U.S. patent application Ser. No. 12/685,289, (U.S. Pat. No. 8,870,797) filed Jan. 11, 2010, which is a divisional application of U.S. patent application Ser. No. 10/973,775, (U.S. Pat. No. 7,645,247) filed Oct. 25, 2004, and claims the benefit of U.S. Provisional Patent Application No. 61/419,525 filed Dec. 3, 2010, the entirety of all of these applications are incorporated by reference.

BACKGROUND OF THE INVENTION

This invention relates generally to the field of cardiovascular medicine, and in particular to the treatment of patients suffering from a spectrum of cardiac states, ranging from shock to pulseless electrical activity, in which the patient appears to be lifeless and in cardiac arrest yet retains some mechanical activity in the myocardial wall motion.

One common technique for treating persons suffering from cardiac arrest is the use of cardiopulmonary resuscitation (CPR). In this procedure, the patient's chest is repeatedly compressed, often in combination with periodic ventilations. Administration of electrical countershock and drugs intended to assist in restoration of cardiopulmonary function to chest compression and ventilation, constitutes advanced life support. For a variety of reasons, the effectiveness of CPR has been limited. Hence, devices or techniques which can improve the effectiveness of CPR are greatly needed.

In additional to sudden cardiac arrest, refractory-shock (which is referred to herein as "shock") is often fatal. For example, if not properly stabilized, a person suffering from shock can progress into cardiac arrest, which, because it is not sudden in nature, is usually fatal. Emergency medicine and critical care practitioners approach the treatment of shock principally by attempting to alleviate the cause because there are no non-invasive techniques that may beneficial in assisting circulation. Hence, devices and techniques are also needed to treat those suffering from refractory shock and shock that is progressing toward cardiac arrest.

There is no general consensus as to when it is the appropriate to start administering CPR as the patient's blood pressure progressively decreases. This relates to a lack of demonstrated efficacy and concern that chest compression may interfere with residual cardiac function, even though CPR may at some point be beneficial in shock patients as they progress to cardiac arrest. Hence there a need for a device or technique to prevent CPR from interfering with residual cardiac function.

Unlike cardiac arrest caused by ventricular fibrillation, pulseless electrical activity (PEA) is a heterogeneous entity with respect to cardiac function and hemodynamics. PEA is a clinical condition characterized by unresponsiveness and lack of palpable pulse in the presence of organized cardiac electrical activity. Pulseless electrical activity has previously been referred to as electromechanical dissociation (EMD). During PEA, electrical activity of the heart may or may not be indicative of cardiac mechanical movements and particularly cardiac output.

Pulseless electrical activity is not necessarily a condition of complete mechanical quiescence in the heart. In PEA, the heart may have a regular organized electrical rhythm such as supraventricular or ventricular rhythms. These cardiac rhythms may not be associated with mechanical activity of the heart in PEA.

As an example of cardiac mechanical patterns during PEA, patients may have weak ventricular contractions and detectable aortic pressure—which is a condition referred as pseudo-PEA. Various studies have documented that between 40-88% of patients with PEA had residual cardiac mechanical activity (pseudo-PEA). In pseudo-PEA, the patient may appear lifeless and without a pulse, despite some degree of residual left ventricle function and hemodynamics. The outcome of patients suffering PEA has tended to be worse than those in ventricular fibrillation, possibly reflecting the potential of CPR chest compressions and residual myocardial mechanical activity to interfere with each other's efficacy. Hence there is a need for a device or technique to enhance the efficacy of CPR in PEA.

BRIEF DESCRIPTION OF THE INVENTION

Disclosed herein are techniques and systems for treating those suffering from a variety of myocardial pathophysiologic states ranging in hemodynamics from awake patients in refractory shock to those who appear to be lifeless, yet who still retain some degree of residual myocardial mechanical function. It has been observed when performing open chest cardiac massage, that coordinating compression and relaxation with the heart's residual mechanical activity often improves recovery of cardiac function. Extrapolating from this, if mechanical myocardial function is present but inadequate, as in PEA, external chest compressions should likely be directed toward assisting cardiac ejection—that is compressing the chest during its intrinsic contractions—and then releasing the chest so as not to interfere with ventricular filling. CPR that is not synchronized with the heart's residual mechanical function may result in application of the compression phase when the left ventricle is trying to fill, resulting in significantly decreased cardiac output on the next ejection secondary to the Frank-Starling Law. Interference with ventricular filling by compression of the chest can be so deleterious that it can, in and of itself, cause complete loss of residual myocardial function resulting in true cardiac arrest.

A system is disclosed here that detects residual myocardial activity in an apparently lifeless patient and outputs signals to trigger chest compressions by mechanical chest compression devices; to audibly indicate when to initiate such chest compressions, or to other interventions that benefit from synchronization with residual myocardial activity. These other interventions may include but are not limited to: abdominal counter-pulsation, ventilation, phasic limb-compression, myocardial electrical stimulation, intravascular fluid shifting, intravascular balloon inflation-deflation, intra-esophageal or intra-pericardial balloon inflation, application of transthoracic electromagnetic irradiation, and the like.

A method is disclosed here for improving the cardiac output of patients suffering from a range of pathophysiologic states such as pulseless electrical activity or shock, which having some residual myocardial wall mechanical activity.

According to the method, residual myocardial activity is sensed to determine the presence of residual ventricular phasic movement, with or without residual left or right ventricular pump function, but having an apparent ejection phase and a relaxation phase. A compressive force is repeatedly applied based on the sensed myocardial activity such that, for example, the compressive force is applied during at least some of the ejection phases and is ceased during at least some of the relaxation phases to permit cardiac filling, thereby creating or enhancing cardiac output and organ perfusion. The synchronization with the sensed myocardial activity may also be used when the patient's chest is actively lifted during decompression. In this way, the chances for improving the outcome of patients suffering from shock or cardiac arrest are improved.

The compressive force may be applied over a variable range of time intervals. For example, the compressive force may be applied for only a certain portion of the contraction or ejection phase, such as at the beginning, middle or end. As another example, the compressive force may be applied during each and every sensed contraction or ejection phase, or only during certain contraction or ejection phases.

The start of the chest compression and the duration of the compression can be adjusted to improve patient outcomes. For example, the adjustments to the start time or duration may be adjusted to optimize the chest compressions or other phasic therapy, where the adjustment is based on feedback of a patient condition or physiologic parameter during one or more prior chest compressions. The feedback signal may, for example, indicate a rate or amount of cardiac ejection or filling, cardiac output or other indicator of mechanical activity of the heart or arterial blood flow. The feedback signal is coupled to the therapy by logic circuits so as to vary the synchronized phasic therapies, e.g., chest compressions, and vary the application of the therapies. By varying the therapies and their application and subsequently re-measuring the feedback signals, the logic circuits can determine which synchronized therapy, or therapies, and pattern of synchronized therapy is optimal and most effective to improve cardiac ejection, cardiac output or otherwise improve the condition of the patient. For example, the logic circuit may vary each of the synchronized therapies and combinations of therapies to determine which pattern of therapy or therapies when synchronized with residual myocardial synchronization results in the greatest measured cardiac output or results in some other measurable condition that indicates that the phasic therapy(ies) are being applied optimally.

Electrical stimulation of the heart may be applied in conjunction with or in addition to chest compressions. The electrical stimulations may be synchronized with electrical signals (ECG/EKG) of the inherent heartbeat, which may be slow and weak, or if there are no regular electrical heart signals, with pulsatile flow or myocardial movements. For example, the electrical stimulation may be synchronized with arterial pulses, such as aortic pressure (AoP), based on detected pulsatile pressure, blood flow, or myocardial movements.

Ventilations are another phasic therapy that may be applied to the patient based on the sensed myocardial activity or hemodynamics. The patient may be ventilated manually or by a mechanical ventilator. The ventilation may be synchronized with chest compressions or other resuscitative therapies in conditions such as shock or pseudo-PEA.

The compressive force may be applied using a variety of devices or equipment. Some examples include mechanical chest compression devices, inflatable vests, nerve stimulators, abdominal compression devices, chest or abdominal active decompression devices, limb phasic compression devices, and the like. Further, the compressive force may be applied at different locations on the chest, abdomen, limbs, or back, such as the left lateral chest, cardiac point of maximal impulse and the like.

The myocardial activity may be sensed using a variety of sensing systems. Such systems may include electrocardiography, Doppler ultrasonography, plethysmography, phonocardiography, echocardiography, transthoracic impedance and the like. These may be incorporated into a probe that is coupled to the chest, abdomen, back, extremities, or a combination of these, or placed within the body, such as within the esophagus, trachea, or stomach. These various types of sensors may detect myocardial activity by detecting, for example, cardiac electrical activity, contractions, other movements of the heart, and palpable pulses of arteries. These measurements may be made from standard locations such as the precordium, but also from the esophagus, trachea, or abdomen. Variations in the skin indicative of pulsating blood flow, and the rhythm and chemical content of the breath, may also be utilized.

The sensors and algorithms optimally suited to sense myocardial activity may depend on characteristics of a particular patient. Further, the sensors optimally suited to sense myocardial activity may change during the course of treating. To determine the optimal sensor or sensors that best indicate myocardial activity, the system may include algorithms to validate the sensor(s) and to correlate sensor output data to a desired patient response, such as improved cardiac output. To validate the sensors, the system may apply or prompt the application of therapies such as chest compressions at a predetermined rate, force or vector and compare the outputs of the sensors to expected sensor outputs or otherwise determine which sensor(s) generate signals that most accurately indicate the response of the patient to the predetermined chest compressions. The validation of sensors results in an identification of sensors and arrangements of sensors that generate signals that most accurately measure or predict the response of the patient. The sensors may be validated at the initiation of therapy and may be revalidated periodically during treatment of the patient, such as at regular intervals or when a substantial change, e.g., beyond a threshold amount, occurs in the response of the patient to treatment.

The validated sensors or validated arrangement of sensors are those sensors that have been determined to most accurately measure or predict a predetermined response(s) of the patient. Once the sensors have been validated, signals generated only by the sensors, or pattern of sensors, identified in the validation process are used to provide feedback to the algorithms that determine the application of phasic therapies such a chest compressions and ventilation. Using these signals, the algorithms may generate and adjust a regimen for chest compressions and ventilations of the patients. The regimen may dictate the force to be applied by the chest compressions, the frequency of the chest compressions, the shape and duration of the force applied by the chest compressions, the synchronization and phasing of the chest compressions with sensed myocardial activity, the location on the chest or other body location, e.g., legs, of compressions, and a vector of the chest or other compressions. The algorithms may vary the regimen to optimize a condition of the patient, such as to increase sensed cardiac output.

In some cases, chest compressions may be performed manually, such as using traditional CPR techniques. In such cases, an audio or visual signal may be produced to indicate when the ejection phase is sensed. The generated signals may indicate to a rescuer when to apply the chest compressions, whether to apply more or less force during the compressions, or whether to apply the compressions to a different location on the chest. In this way, the rescuer will be prompted as to when, how and where to apply the compressive force to the patient. The tone, volume, or other parameter, of the synchronizing prompt may be varied so as to assist the rescuer in providing optimal CPR. In some cases, the chest, abdomen, or extremities may also be actively or passively compressed or decompressed in an alternating manner with chest compressions, and in synchronization with either cardiac ejection or filling.

A system is disclosed here for improving the cardiac output and prognosis of a patient who is suffering from impaired myocardial mechanical states such as pulseless electrical activity or shock but having residual myocardial wall motion. The system comprises a myocardial activity sensor that is adapted to sense movement of the myocardial wall and or myocardial valvular motion to determine the presence of residual ventricular contract and relaxation, and/or pump function having an ejection phase and a filling phase. The system may also include a compression device that is configured to repeatedly apply a compressive force to the heart, either through the chest wall, intrathoracically through the pericardium, or directly to the myocardium through an endoscope and pericardial window. Further, a controller is employed to receive signals from the myocardial activity sensor and to control operation of the compression device such that the compression device repeatedly applies a compressive force to the heart such that the compressive force is applied during at least some of the ejection phases and is ceased during at least some of the relaxation phases to permit residual cardiac filling, thereby enhancing cardiac output and organ perfusion.

As an option to using a mechanical compression device or as an initial treatment applied before the compression device is setup on a patient, chest compressions may be performed manually. In such cases, the system may include a cadence device that is configured to produce audio and/or visual signals indicative of when compressive forces are to be applied and ceased. This same cadence system may be utilized to synchronization other therapies phasic therapies such as ventilation or abdominal counterpulsation.

The myocardial activity sensors that may be used include electrocardiography sensors, Doppler ultrasonography sensors, plethysmography sensors, phonocardiography sensors, echocardiography sensors, transthoracic impedance sensors, magnetic resonance imaging, and radiographic fluoroscopy. These sensors may be placed on the patient's chest, abdomen, back or extremities, within body cavities such as the esophagus, or some distance from the patient in the case of technologies like radiography or magnetic resonance imaging. If the patient has an arterial pressure catheter in place, the controller may also utilize that signal for synchronization. Further, the controller may be configured to apply the compressive force during each sensed ejection phase or during only at certain ejection phases. As another option, the controller may be configured to apply the compressive force for only a certain duration of the ejection phase.

The system may further include a ventilator device that is configured to provide ventilation to the patient based on the sensed residual myocardial mechanical activity. The controller may also vary the pattern of individual ventilations so as to optimize synchronization.

A sensor may detect the expansion and relaxation of the chest due to ventilation or chest compressions. The sensor may be a plastic adhesive strip applied to the chest that stretches and contracts with the movement of the chest due. The stretch and contraction of the adhesive strip may be detected as a change in an electrical property, e.g., resistance, of the strip, optically due to a change in transmissivity or reflection of the strip or by other means. The stretch and contraction of the adhesive strip causes the adhesive strip sensor to generate signals indicative of the expansion and relaxation of the chest. These signals may be used by the algorithms to predict when blood is being drawn into the heart as the chest relaxes (expands) or when blood is being forced from the heart as the chest is compressed.

The phasic device may be a mechanical compression device, an inflatable vest, a nerve stimulator, or the like. Further, the system may include a lifting device that is configured to actively decompress the chest during the relaxation phase, or compress the abdomen during chest decompression.

In another embodiment, a logic circuit may be used to vary the phasic therapeutic device or devices such that the optimal pattern and combination can be determined and applied. This pattern may be variable over time and the invention will monitor for the possibility by occasionally varying the pattern of therapies and adjusting according to an indicator of hemodynamics or predictor of outcome.

During resuscitation of patients suffering cardiac arrest, the presence and degree of residual left ventricular mechanical (physical) activity may vary over time. The system may be configured to detect transient periods of left ventricular mechanical activity and to synchronize therapies only during these periods to assist residual cardiac mechanical activity and achieve a greater cardiac output.

The sensor functions may be utilized to determine the vector of left ventricular ejection and to optimize the force vector of chest compression spatially. This might be done utilizing an array of Doppler probes placed over the chest to detect the velocity of residual myocardial motion from multiple locations and calculate the vector of that motion.

The vector of left ventricular blood flow ejection is generally from the point of maximal impulse in the left lateral chest between 4th and 6th intercostal spaces near the lateral clavicular line toward the medial cephalad direction. The system disclosed here can determine the vector and align the force of chest compression with the vector to assist ejection of blood and minimize interference with ventricular filling.

Utilizing an indicator of cardiac output, such as exhaled end-tidal carbon dioxide or vital organ oxymetry, the controller circuit could apply synchronized therapies during progressive shock and determine if they benefit the patient through increased blood flow.

A system is disclosed here to treat a patient having a heart and a chest, the system comprising: a least one sensor monitoring cardiac activity in the patient by detecting at least one of myocardial pump activity, myocardial mechanical activity, hemodynamics and organ perfusion; a logic controller receiving signals from the at least one sensor and generating control commands for controlling one or more phasic therapies and synchronizing the one or more phasic therapies with the monitored cardiac activity in the patient; and wherein the logic controller executes an algorithm stored in memory associated with the logic controller, wherein the algorithm causes the logic controller to generate commands to vary patterns of the application of the one or more phasic therapies, and thereafter detect changes in at least one of the sensed myocardial pump activity, myocardial mechanical activity, hemodynamics and organ perfusion due to variations in the patterns, and determine one of the patterns of phasic therapies corresponding to a desired level of at least one of sensed myocardial pump activity, myocardial mechanical activity, hemodynamics and organ perfusion hemodynamics and organ perfusion.

A method is disclosed here to treat a patient in shock comprising: sensing myocardial motion or pulsatile blood flow in the patient; repeatedly applying a phasic therapy to the patient synchronized to the sensed actual myocardial motion or pulsatile blood flow, wherein the phasic therapy includes repeatedly applying a compressive force to the chest or an electrical shock to the heart of the patient, and adjusting the compressive force or electrical shock depending on whether the force or shock coincides with a heart beat as indicated by sensed myocardial motion or pulsatile blood flow.

A system is disclosed here to treat a patient having a heart and a chest, the system comprising: a least one sensor monitoring cardiac activity in the patient by detecting at least one of myocardial pump activity, myocardial mechanical activity, hemodynamics and organ perfusion; a logic controller receiving signals from the at least one sensor and generating control commands for controlling one or more phasic therapies and synchronizing the one or more phasic therapies with the monitored cardiac activity in the patient; and wherein the logic controller executes an algorithm stored in memory associated with the logic controller, wherein the algorithm causes the logic controller to generate commands to vary patterns of one or more phasic therapies, and thereafter detect changes in at least one of the sensed parameters due to variation in the pattern of phasic therapies. The logic circuit would then determine which one of the patterns of phasic therapies corresponding to a desired level of at least one of sensed myocardial pump activity, myocardial mechanical activity, hemodynamics and organ perfusion hemodynamics and organ perfusion.

A method is disclosed here to treat a patient comprising: sensing a natural rate of myocardial activity of the heart of the patient, and repeatedly applying a phasic therapy to the patient synchronized to the sensed myocardial activity, wherein the phasic therapy includes repeated myocardial electrical stimulation applied at a rate faster than the sensed natural rate of myocardial activity. The method may further comprise a sensing system comparing at least one of the sensed myocardial pump activity, myocardial mechanical activity, hemodynamics and organ perfusion hemodynamics and organ perfusion with and without application of the phasic therapies to determine which of the phasic therapies optimally augments hemodynamics or perfusion.

A method is disclosed here to treat a patient having a heart and a chest, the system comprising: monitoring cardiac activity in the patient by detecting with at least one sensor at least one of myocardial pump activity, myocardial mechanical activity, hemodynamics and organ perfusion; receiving the signals from the at least one sensor and, based on the signals, synchronizing one or more phasic therapies applied to the patient to the monitored cardiac activity in the patient; varying the one or more phasic therapies; detect changes in at least one of the sensed myocardial pump activity, myocardial mechanical activity, hemodynamics and organ perfusion due to the variations in the one or more phasic therapies; determine one of the variations of the phasic therapies corresponding to a desired level of at least one of sensed myocardial pump activity, myocardial mechanical activity, hemodynamics and organ perfusion hemodynamics and organ perfusion.

The method may further comprise comparing at least one of the sensed myocardial pump activity, myocardial mechanical activity, hemodynamics and organ perfusion with and without application of the phasic therapies to determine which of the phasic therapies optimally augments hemodynamics or perfusion.

DETAILED DESCRIPTION

Figure 1:
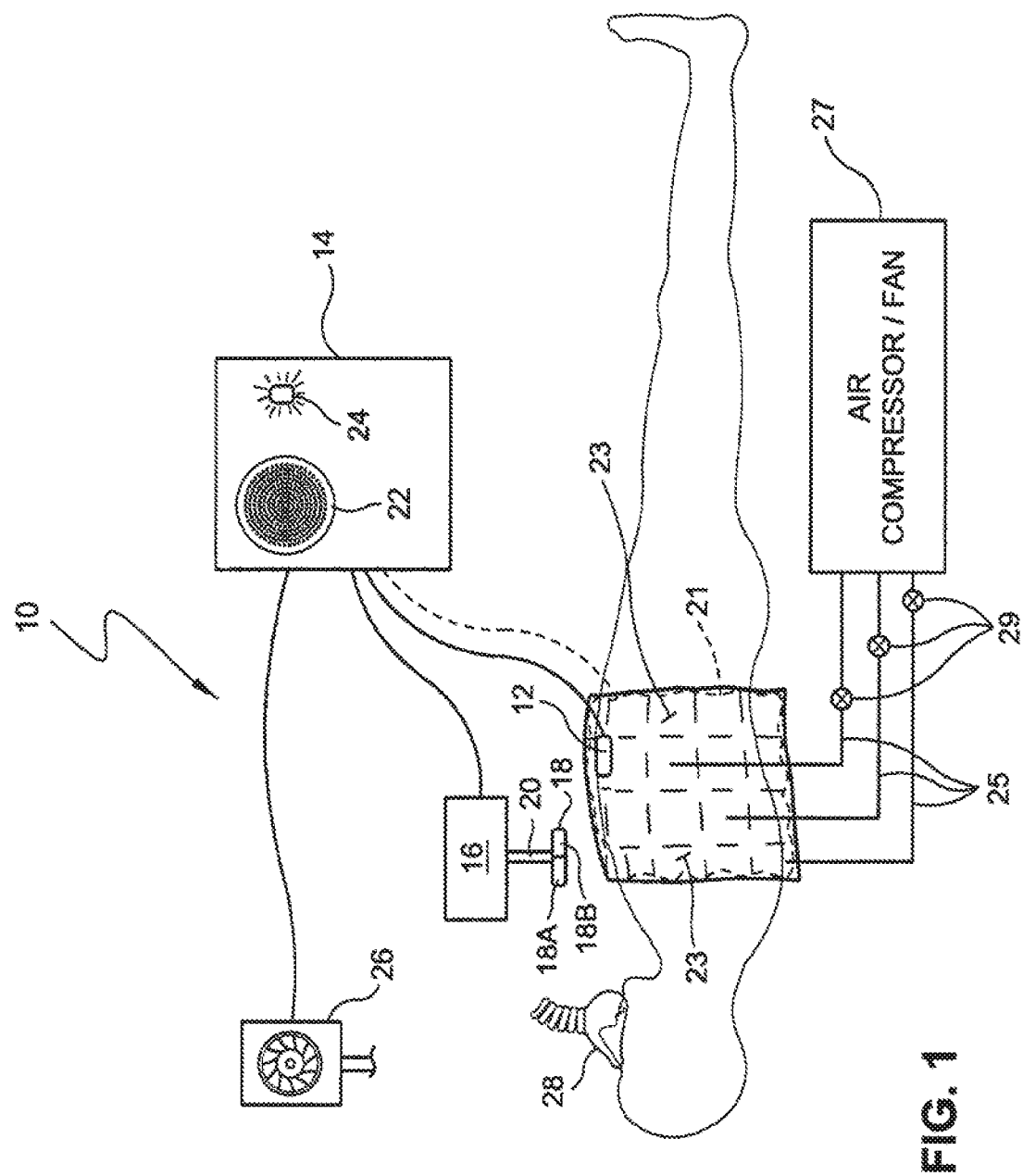
FIG. 1 is a schematic view of a system that may be used to improve the cardiac output of a patient according to the invention.

The invention relates to techniques and devices that may be used to increase cardiac output for patients suffering from a wide variety of ailments ranging from shock to pulseless electrical activity (PEA) where the patient appears to be lifeless yet has some residual mechanical heart activity. One exemplary technique of the invention is to sense when the heart is beating and then synchronize chest compressions, or other resuscitative techniques, with movement of the myocardial wall. In this way, various techniques may be used to optimally synchronize chest compressions (or other elements of CPR) with residual left ventricular function to improve the outcome of such patients. Hence, the invention may be used to synchronize the compression force of external devices, on or around the chest, with the ejection phase of the residual left ventricular function, and the relaxation phase with residual cardiac filling. In another aspect, the system and method disclosed herein provides various techniques and devices for sensing residual mechanical function, and then turn this information into a useful data stream that may be used to operate the various components of resuscitative technology, including adjuncts to blood flow, ventilation, and cardiac stimulating technology.

Such techniques may be used with patients suffering from a wide range of ailments. One exemplary use is for patients who are believed to be in cardiac arrest with pulseless electrical activity (PEA) and non-detectable blood pressures, but who still have residual left ventricular function to some degree. However, it will be appreciated that the invention is not intended to be limited to only such a use, but to a wide range of conditions where there is some organized electrical (but impaired) mechanical cardiac activity.

For example, at one end of such a spectrum is normal spontaneous circulation, where the cardiac outputs are normal and left ventricular mechanical and pumping function are normal. Below that level is hypotension then compensated shock. In such cases, the blood pressure and the patient's pulse are still palpable and there may be good cardiac output. However, for various reasons, the cardiac output is unable to meet the metabolic demands of the body and homeostasis is at risk. This is evident by parameters such as decreasing urine output and increasing serum lactate, which are markers of inadequate organ function.

Below compensated shock is the state of uncompensated shock. This is a state in which the myocardium and the cardiovascular system are no longer able to provide adequate amounts of blood flow, oxygen and nutrients to meet the needs of vital organs, and the function of those organs is affected to the extent that they are beginning to become damaged. Blood pressures in this state might be, for example, 70/30 mm Hg. systolic over diastolic. Also, urine output may cease, and the patient may become confused because of inadequate cerebral function. Importantly, as shock progresses, the pathways to multi-organ system failure are initiated.

Below classical uncompensated shock is what might be called "extreme shock" which borders on cardiac arrest. In this case, the patient exhibits some residual myocardial function including some left ventricular ejection, but cardiac output is wholly inadequate to meet the needs of vital organs. For example, cardiac output might be less than 1 liter per minute, blood pressure might be 50/20, urine output may be minimal or absent, and the patient may be stuporous or comatose. Further, the patient may appear to be near death with significantly impaired cerebral function and stupor bordering on coma. If untreated, extreme shock will result in true cardiac arrest in a timeframe of minutes. Generally, it is not possible to palpate arterial pulses manually in this range, and such patients may be classified as PEA by clinical personnel even thought their heart continues to beat.

Below the state of extreme shock is pulseless electrical activity (PEA) cardiac arrest, which importantly also has a spectrum of conditions and a range of hemodynamics. For example, at its upper end, PEA has both left ventricular mechanical function and cardiac output, but not sufficient enough to be detected as a peripheral radial or femoral pulse. If an intra-arterial catheter is placed into the patient, the blood pressure might be only 45/25, with blood pressure measurable only in major arteries of the chest, neck or groin. A Doppler probe placed over the neck or groin may detect forward blood flow. Blood flow is so profoundly inadequate that the patient will generally appear lifeless and their pupils may dilate and become fixed. Further, they appear to be in cardiac arrest despite the presence of residual pump function and forward flow. The high end of PEA dynamics overlaps the low end of "extreme shock." In such cases, the clinical personnel may not be able to distinguish the differences. The electrocardiogram, while showing organized electrical activity, is variable in its pathology and may be relatively normal in its QRS configuration. The inventor has termed electromechanical dissociation (EMD) with residual myocardial mechanical activity "pseudo-EMD."

Below the "high end" stage of PEA is electromechanical dissociation with almost absent left ventricular function. The blood pressure measured by intravascular catheters just above the aortic valve will show aortic pulsations but the blood pressures measured are on the order of 25/15 mm HG, and there will be almost no associated forward blood flow. Without application of CPR, oxygen delivered to the vital organs will be essentially absent and irreparable injury to organs such as the brain occurs within minutes. The electrocardiogram rarely has a normal appearing QRS configuration, and the overall pattern of the ECG may be slurred out and irregular.

The final stage of PEA is an organized electrical rhythm but no left ventricular mechanical function. This is true cardiac arrest. A catheter measuring pressures above the aortic valve will detect no pressure pulse and echocardiography will show no cardiac movement. Further, the cardiac output is 0 and the patient is in complete global ischemia and cardiac arrest. Without application of CPR, oxygen delivered to the vital organs will be 0, and irreparable injury to organs such as the brain occurs within minutes. The overall pattern of the ECG is invariably slurred out and irregular.

Along the spectrum described above, the invention may be used in all cases where there is some myocardial mechanical activity and synchronized resuscitative therapies may improve cardiac output. In such cases, the invention may be used to detect residual mechanical activity and to synchronize such activity of the heart with resuscitation techniques, such as those used in CPR (including chest compressions/decompressions and/or ventilation). Hence, the invention may be utilized in any pathophysiologic state from true cardiac arrest, to pseudo-EMD PEA, through the various stages of shock, or in any hemodynamics state in which residual myocardial mechanical function with and without cardiac output exists. By synchronizing chest compressions and/or decompressions, among other potentially cyclical therapies, both ejection and filling phases of the cardiac cycle may be augmented. In so doing, cardiac output and organ profusion may be increased, thereby improving the outcome of patients with impaired hemodynamics.

As one particularly important example, one clinical situation that often occurs and is challenging for physicians, is when patients progress from shock to apparent PEA cardiac arrest. In the earlier stages of this process, physicians tend to treat such patients with intravenous medications and possibly controlled ventilation. While drugs such as antibiotics may be administered to patients in states such as septic shock, pressor drugs such as dopamine continue to be a mainstay of treatment. Pressors, however, have generally not been shown to improve the outcome of such patients despite raising the blood pressure. This may be because they improve blood pressure but also raise vital organ oxygen utilization, such that the overall balance between oxygen supply and demand is not improved. Pressor drugs also have significant direct vital organ toxicity.

If, however, these parenteral therapies do not stabilize the patient, their shock may progress inexorably towards more and more extreme states and eventually become cardiac arrest. Many practitioners in emergency medicine and critical care continue to be unsure—and the medical literature remains unclear—as to which point a patient whose blood pressure is dropping should begin to receive chest compressions. Indeed, physicians generally do not apply techniques such as external chest compress before subjective loss of vital signs. This is because CPR, and in particular chest compressions, can interfere with cardiac function and in particular cardiac filling if applied in an unsynchronized manner. For instance, a patient whose blood pressure is 60/40 who begins to receive chest compressions out of synchronization with heart function could rapidly progress into full cardiac arrest. More specifically, in performing CPR without synchronization, application of the compression phase when the left ventricle is trying to fill may significantly decrease cardiac output on the next ejection secondary to the Frank Starling Law of the heart. Hence, by detecting myocardial mechanical function, chest compressions can be synchronized with the ejection phase so that patients in shock may be treated without exacerbating their condition and possibly moving them toward cardiac arrest.

Hence, the issue as to when chest compressions should begin when a patient is progressing through the stages of shock may be addressed by synchronizing chest compressions, and possibly other mechanical adjuncts, with the ejection and relaxation phases, so that the clinician may be more confident that chest compressions are assisting and not interfering with residual circulatory function. In this way, the clinician does not need to be as concerned with the question as to when to begin chest compressions. In this manner, the invention may act to allow use of external mechanical adjuncts in the treatment of any form of shock in a manner similar to the methods by which intra-aortic balloon counterpulsation has been applied in cardiogenic shock. The invention may thus allow application of such adjuncts in the pre-hospital, and Emergency Department environments.

Another advantage of using synchronization is that it may be performed as an adjunct to therapies directed at the cause of the shock, such as antibiotics or thrombolysis, enhancing vital organ perfusion while these therapies are being administered. Indeed, improved hemodynamics may not only stave off organ injury, it may improve the efficacy of parenteral therapies. Further, synchronized chest compressions are unlikely to have significant organ toxicity, unlike pressor drugs.

As described above, one particular application of the invention is in connection with those suffering from pulseless electrical activity (PEA). PEA is one of the three broad-types of cardiac arrest, the other two being ventricular fibrillation and asystole. PEA is also referred to as electromechanical disassociation (EMD). PEA has been described as "the presence of organized electrical activity on the electrocardiogram but without palpable pulses." Rosen P, Baker F J, Barkin R M, Braen G R, Dailey R H, Levy R C. Emergency Medicine Concepts and Clinical Practice. 2nd ed. St Louis: CV Mosby, 1988. Unlike ventricular fibrillation, which can be specifically reversed with electrical countershock, PEA does not have a specific countermeasure. This may explain the traditionally worse outcome of patients in PEA compared to ventricular fibrillation. Unfortunately, the incidence of PEA is increasing, possible because early risk modification is changing the natural history of cardiovascular disease. It is now reported by some authorities that the majority of patients in cardiac arrest are in PEA at the time of EMS arrival. Additionally, a significant fraction of patients that are shocked out of ventricular fibrillation, or resuscitated from asystole, will experience PEA at some point during their resuscitation. The combination of these circumstances mean that a large majority of patients receiving advanced life support for treatment of cardiac arrest will have PEA at some time during resuscitation. Hence, now or in the near future PEA may supersede classical ventricular fibrillation in importance. It may already have done so.

Many patients with PEA have residual cardiac mechanical activity, and many have detectable blood pressures. This condition may be referred to as pseudo-EMD PEA. In such cases, the patient may appear lifeless and without a pulse. However, there often remains some degree of residual left ventricular function. Hence, one important feature of the invention is to sense when the patient still has some myocardial function and then to synchronize phasic resuscitation therapies, especially compression of the chest, with the heart's residual mechanical function. In this way, the compression phase of CPR may occur during the ejection phase, and the relaxation phase can allow elastic recoil of the chest—with associated decreases in intrathoracic pressure when the left ventricle is trying to fill. In this way, synchronizing phasic resuscitative therapies with residual ventricular ejection and filling, may improve hemodynamics, the rate of a return to spontaneous circulation (ROSC), and long term survival.

The invention may incorporate various non-invasive sensing technologies (represented by sensor 12 in FIG. 1) to acquire real-time data describing the pattern of myocardial wall and or valve motion so as to allow synchronization of chest compressions and other therapies. If, however, invasive indicators of hemodynamics, such as intra-arterial pressure or flow monitors, are present, then the invention may act as an interface between those inputs and phasic resuscitative therapies as exemplifies by external chest compression. To apply proper synchronization between the forces of external devices, on or around the chest or body, and the ejection and filling phases of residual left ventricular function, a variety of devices may be used. The decision that residual myocardial activity exists may be made from a logic circuit with inputs from multiple sensing modalities. The invention may utilize sensing technology to collect the data on myocardial wall function, myocardial valve motion, blood flow in vascular structures, vital organ oxygen or energy status, or exhaled pulmonary gas, and this data may be passed through logic circuits and a controlling output signal passed to the devices that deliver therapies. Because the pattern of mechanical residual wall function may be variable over time, the invention may be designed to promptly identify residual function and to vary therapeutics based on feed back to a logic circuit. Also, the synchronizing of external chest compressions may be used with other techniques, such as with abdominal counter pulsations, phasic limb compression, ventilation, and electrical stimulation, among others, to augment cardiac ejection and filling. In this way, the patient may be stabilized to allow sufficient time for primary therapies, such as thrombolysis, to be effective.

A wide variety of equipment and device may be used to provide chest compressions. For example, various types of automated compression systems may be use to compress the chest. These include systems, such as the AutoPulse Resuscitation System, by ZOLL Circulation, Inc. of Sunnyvale, Calif., the Thumper manufactured by Michigan Instruments or the LUCAS device, and the like. Further, the invention is not limited to automated compression systems, but may be used with manual techniques as well. For example, the invention may be used to provide an audio and/or visual signal to indicate to a rescuer as to when to manually apply chest compressions. Further, in some cases a suction device may be adhered to the chest so that the chest may be actively lifted intermittently with chest compressions.

Using either manual or automated equipment, the invention may be configured to synchronize external chest compressions with any residual mechanical activity of the myocardium such that when the myocardium enters pumping or systole phase, CPR is in the chest compression phase.

Further, when the heart enters its refilling or diastole phase, chest compressions enter the relaxation phase. Sensory data may be passed through a logic circuit and outputs of that circuit used to control when during cardiac ejection or filling of synchronization occurs. These relationships may be varied over time to optimize the efficacy.

In addition to synchronizing chest compressions with residual heart function, the invention may also be use to synchronize ventilations with residual heart function. For example, inspiration and expiration may be synchronized with residual myocardial function so as to increase cardiac output. For instance, inspiration may be synchronized to systole and expiration with diastole. To apply ventilations, the invention may use a traditional ventilator or ventilations may be provided manually, such as by using a ventilatory bag. In the latter case, an audio and/or visual signal may be provided to the rescuer as to when to apply proper ventilations.

With both chest compressions and ventilations, the timing, frequency and/or duration may be varied depending on the particular treatment. For example, chest compressions may occur during the entire systole phase, or only during a portion of it. Further, chest compressions may occur every systole phase or during only certain systole phases. A similar scenario may occur with ventilations. The controller may use one or more sensory inputs, and a logic circuit utilizing and indicator or indicators of efficacy, to optimize the effect of synchronization on hemodynamics.

The system disclosed herein may be utilized with any therapy that may benefit from synchronization with residual myocardial mechanical function in apparently lifeless patients. Chest compression and decompression, abdominal counter-pulsation, ventilation, phasic limb-compression, myocardial electrical stimulation, intravascular fluid shifting, intravascular or intra-pericardial balloon inflation-deflation, application of transthoracic electromagnetic irradiation, among others. The controller logic circuit may vary the pattern of synchronization among multiple therapies so as to determine the optimal pattern with respect to increasing hemodynamics.

Myocardial electrical stimulation is, for example, external electrical shocks delivered through metal paddles or electrodes applied to the chest, or electrical signals applied directly to the heart from an internal pacemaker modified to synchronize myocardial electrical stimulations to, for example, myocardial wall function or detected pulsatile blood flow.

To sense myocardial wall function, a variety of noninvasive devices and technologies may be used. For example, one technology that may be used is electrocardiography (ECG). ECG may be an attractive detection method because it is already used in most clinical situations during resuscitation. However, because myocardial activity is not always present with ECG during PEA, it may need to be used in combination with other sensing techniques as described below. Another example of a sensing technique that may be used is Doppler ultrasonography (DOP). Doppler ultrasound uses the Doppler shift of ultrasonic wave to quantify the blood flow in peripheral vessels. This may be applied with a transducer on the neck for carotid flow, the groin for femoral flow, or a transthoracic or intraesophageal transducer for aortic flow. A Doppler probe may also be placed at the cardiac point of maximum impulse to detect movement of blood within the myocardium. An array of Doppler probes may be used to determine the vector of residual myocardial mechanical function and align chest compression and relation with that vector.

A dynamic pressure sensor detects pulsatile flow by sensing the oxygen content in a peripheral vein. The oxygen content sensed by the ROSS sensors as blood pulses through the peripheral vein. Similarly a pulse oximetry sensor may also be used to detect the oxygen content in a blood vessel in, for example, the toes, fingers or ear lobes. The oxygen content of the blood may be used to determine when to initiate and terminate CPR and mechanical or electrical cardiac stimulation. For example, if the ROSS sensor or pulse oximetry sensor detects pulsatile flow and an oxygen content above a threshold, the system may reduce the force of chest compressions or terminate chest compressions. Similarly, if the ROSS or oximetry sensor detects no pulsatile flow or an oxygen level falling below a threshold, the system may initiate manual chest compressor or electrical cardiac stimulation. The system may adjust various parameters of phasic therapies based on trends in the sensed oxygen status.

The data regarding pulses in peripheral blood vessels may be utilized to estimate residual myocardial mechanical function, such as the cardiac ejection phase, based on stored information regarding the delay between the myocardial mechanical function and pulse pressure or pulsatile flow in the peripheral blood vessel.

A further sensing technique that may be used is plethysmography (PLETH). Plethysmography may be applied by measuring changes in the transthoracic AC electrical impedance with heart motion. A further technique that may be used is phonocardiography (PHONO). Phonocardiography records the acoustical energy detected by a stethoscope over the heart. Still a further technique that may be used is echocardiography (ECHO). With echocardiography or ultrasound imaging of the heart, left ventricular ejection can be quantified. In some cases, echocardiograph detection of heart function may be combined with ECG. Also, sensitivity may be improved through the use of intravenously injected microbubbles or other ultrasound enhancing technologies.

It may be optimal to combine a number of these detection systems so as to increase the sensitivity and specificity of detecting residual myocardial mechanical function. Additionally, it may be optimal to incorporate a logic circuit which compares combinations of sensing technologies to an indicator of actual cardiac output, such as end-tidal carbon dioxide or aortic flow. In this manner, the invention could determine which combination of sensing technologies are most predictive of improvements derived from synchronization.

Additionally, the logic circuit of the invention might be capable of varying the synchronized therapeutics against indicators of actual cardiac output so as to determine which pattern of synchronized therapy is most effective. It may vary synchronization within one therapeutic device or multiple therapeutic devices so as to identify the optimal pattern.

Referring now to FIG. 1, a system 10 for improving cardiac output will be described. System 10 includes a sensor, or sensors, 12 that may be used to detect residual myocardial mechanical function. In one embodiment, sensor 12 may comprise a surface probe that rests on the patient's chest. Sensor 12 may be placed at a variety of locations on the chest. For example, one location may be the anterior chest in one of the intercostal spaces. Another location may be the sub-xiphoid location in the epigastrium. Sensor 12 may sense myocardial wall motion using any of the technologies described herein, including ultrasound, Doppler technology, echocardiography, plethysmography and the like. As an alternative to placing sensor 12 on the patient's chest, it will be appreciated that other locations may be used as well, such as a probe that is placed on the neck over the carotids, or into the patient's esophagus. It will also be appreciated that sensor 12 may be an array of sensors.

The sensor 12 may be a sensor or sensors for a variety of sensing systems such as electrocardiography, Doppler ultrasonography, plethysmography, phonocardiography, echocardiography, transthoracic impedance and the like. The sensor 12 may be incorporated into a probe that is coupled to the chest, abdomen, back, extremities, or a combination of these, or placed within the body, such as within the esophagus, trachea, or stomach. These various types of sensors detect myocardial activity by detecting, for example, cardiac electrical activity; physical contractions and other movements of the heart, palpable pulses of arteries in, for example, the esophagus, trachea, or stomach; variations in the skin indicative of pulsating blood flow and the rhythm and chemical content of the breath.

The data collected by sensor 12 is transmitted to a controller 14 having signal processing and logic capabilities. A further description of controller 14 will be described hereinafter with reference to FIG. 2. Controller 14 is also electronically coupled to a compression device 16 that may be used to apply external chest compression to the patient. In some embodiments, it will be appreciated that controller 14 could be incorporated into compression device 16 or into any of the sensors. For ease of use, both the sensor 12 and the controller 14 may be incorporated into the therapy device 16. Further, controller 14 could be wirelessly connected to the sensing and/or compression devices. In the example illustrated in FIG. 1, chest compression device 16 includes an interface member 18 that is coupled to a piston 20 which moves interface member 18 against the chest in a repeating manner. In this way, chest compression device 16 may apply repeating chest compressions to the patient. In some cases, interface member 18 may be configured to adhere to the patient's chest so that as piston 20 lifts interface member 18, the patients' chest will also be lifted. In this way, chest compression device 16 may apply alternating chest compressions and decompressions. Although described in the context of chest compression device 16, it will be appreciated that a wide variety of equipment may be used to apply chest, abdomen or extremity compressions and/or decompressions in an automated manner as described herein, and that the invention is not intended to be limited to only the specific embodiment of chest compression device 16. For instance, examples of existing CPR equipment that may be modified to function in connection with controller 14 include the AutoPulse Resuscitation System by Revivant of Sunnyvale, Calif., or the Thumper manufactured by Michigan Instruments. As another option, an inflatable vest 21 may be coupled to controller 14 and be configured to be inflated and deflated to perform proper synchronization.

As an alternative to applying automated chest compressions, the invention may also be used with manual techniques. In such cases, controller 14 may include a speaker 22 and/or a light 24 that provide information to a rescuer as to when to apply chest compressions and/or decompressions. For example, speaker 22 may be configured as a metronome to apply a repeating signal, or could give instructions in a human understandable voice. Light 24 may be configured to repeatedly flash to indicate when to apply chest compressions and/or decompressions. It will also be appreciated that a force transducer may be placed between the hands of the person providing manual chest compression and the patients such that the force, timing and vector of chest compression can be sensed so that the accuracy of synchronization is evaluated.

Chest compressions may be applied at a variety of locations. Examples include the sternal area, parasternal areas, circumferentially, the back, and the like. The abdomen may be compressed or counterpulsed broadly or with specific emphasis on the areas of the abdominal aorta or inferior vena cava. The extremities may be compressed rhythmically. The pattern of ventilation may be varied.

Controller 14 configured to receive data from sensor 12 and then process the signals in order to operate chest compression device 16, speaker 22 or light 24. More specifically, controller 14 is configured to synchronize external chest compressions and/or decompressions with any residual mechanical activity of the myocardium sensed by sensor 12. In this way, when the myocardium enters the pumping or systole phase, chest compression device 16 is configured to force interface member 18 against the chest to apply a chest compression. When the heart enters its refilling or diastole phase, controller 14 is configured to lift interface member 18 so that no compressive forces are being applied to the chest. It is understood that the therapeutic impulses may be restricted to a portion of each phase.

The vest 21 may include separately inflatable chambers 23 wherein each chamber is coupled via a conduit 25 to an air pump 27. Valves 29 in the conduits are actuated by the controller 14 to cause the inflation and deflation of the chamber associated with the valve. By selectively inflating and deflating the chambers, specific locations on the chest and back of the patient that are compressed can be to enhance the chest compressions and increase the cardiac output. As an alternative to a vest with chambers, the chest compression device may include a force interface member 18 that is segmented into a plurality of separately actuated pads 18a, 18b applied to compress the chest. Depending on which of the pads 18a, 18b are actuated to compress the chest and the sequence in with one or more of the pads are actuated the position on the chest of the chest compressions and the vector of the force applied by the chest compression can be varied to enhance, for example, cardiac output.

System 10 further includes a ventilation system 26 that is coupled to controller 14. For example, ventilation system 26 may comprise a ventilator that is in fluid communication with a mask 28. Controller 14 may be configured to synchronize inspiration and expiration to residual myocardial function as detected by sensor 12. For example, ventilation system 26 may be configured to provide positive pressure ventilations during systole and allow for expiration during diastole, or vice versa. Controller 14 may also be configured to coordinate operation of ventilation system 26 with chest compression device 16. As an option to using a mechanical ventilator, the invention may also utilize other techniques, such as a ventilatory bag that may be mechanically squeezed by the patient. In such cases, speaker 22 or light 24 may be actuated to indicate to the rescuer as to when to apply proper ventilations.

Figure 2:
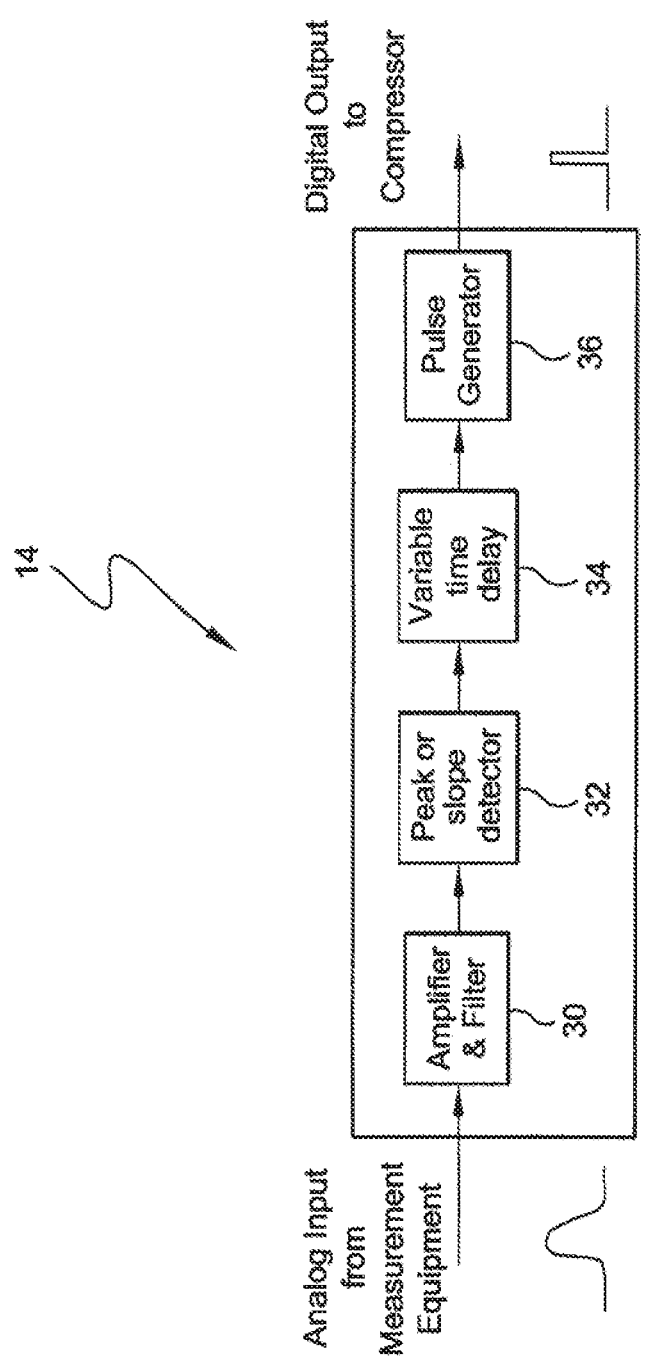
FIG. 2 is a schematic diagram of a controller that may be used to actuate a compression device based on signals from a myocardial activity sensor according to the invention.

Referring now to FIG. 2, one aspect of controller 14 will be described in greater detail. As previously described, controller 14 receives signals from sensor 12 regarding residual myocardial wall function. Typically, signals from sensor 12 will be in analog form. As such, controller 14 may include an amplifier and filter 30 which amplify and filter the analog signal. Controller 14 also includes a peak or slope detector 32 which is circuitry that detects either peaks or slopes of the analog signal that are indicative of myocardial wall motion. Detector 32 may be configured to trigger on rapid increases in signal amplitude. The triggered signal from detector 32 will pass through a variable time delay circuitry which is fed to a pulse generator 36 that converts the analog trigger into a digital pulse of fixed amplitude and duration. The variable time delay 32 may be added to this pulse to allow for fine adjustment of synchronization in timing. The delayed pulse is then processed as an output to chest compression device 16 in digital format.

The controller may combine inputs from a number of sensing systems so as to increase the sensitivity and specificity of detecting residual myocardial mechanical function. Additionally, it may be optimal to incorporate a logic circuit, possibly within a microprocessor, which compares combinations of sensing technologies to an indicator of actual cardiac output, such as end-tidal carbon dioxide or aortic flow. In this manner, the invention could determine which combination of sensing technologies are most predictive of improvements derived from synchronization. Additionally, the logic circuit of the invention might be capable of varying the synchronized therapeutics and comparing the combinations to amount of residual myocardial synchronization and measured cardiac output so as to determine which pattern of synchronized therapy is most effective.

Figure 3:
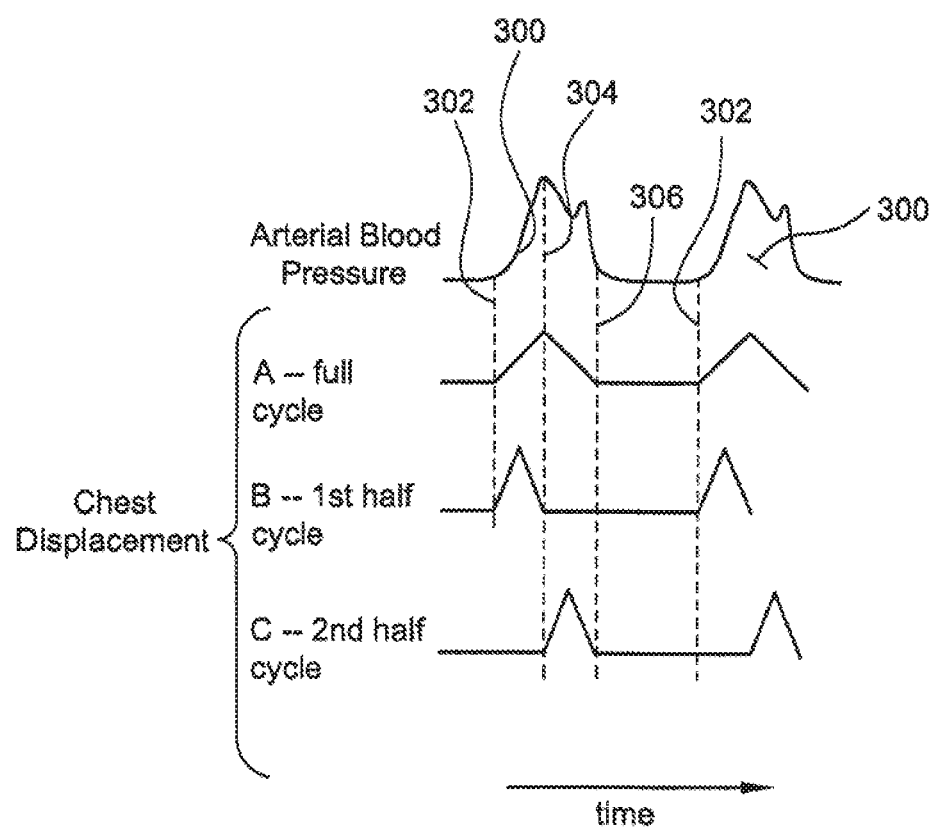
FIG. 3 is a graph illustrating exemplary times for applying compressive forces according to the invention.

As previously mentioned, chest or abdominal compressions and/or ventilations may be applied during different times of the cardiac cycle and may be varied over the cycles themselves. The arterial blood pressure shown in FIG. 3 represents the pulsatile flow as indicated by the increase in arterial blood pressure for each pulse 300. The dotted lines in FIG. 3 refer to an initial increase or predetermined change to an upward slope 302 in arterial blood pressure, a peak pressure 304 and an end of the pressure pulse, such as represented by a predetermined change to a downward slope of the pressure. For example, as illustrated in FIG. 3, a chest compression may be applied each time the sensor detects the ejection phase, and this compression may occur throughout the entire ejection phase as shown in A—Full Cycle portion of FIG. 3. Alternatively, the chest compression could be applied only during the first half of the ejection cycle as shown in B—$1^{st}$ Half Cycle. As another option, the chest compression could be applied during the second half of the ejection cycle as shown in C—$2^{nd}$ Half Cycle. As a further alternative, chest compressions could be applied during each ejection cycle, or only during certain ejection cycles, such as every second, third, or fourth ejection cycle. Also, the magnitude of chest compressions may be evaluated to determine if they should be increased or decreased throughout the procedure. A similar scenario may be used for chest decompressions, abdominal compression decompression or counterpulsations, limb compressions, and the phases of ventilations.

In summary, by utilizing a sensor, or combination of sensors, an apparently lifeless patient's residual myocardial wall function may be detected and the application of phasic resuscitative therapies, including chest compressions and/or decompressions as well as abdominal counterpulsations, and ventilations may be precisely controlled so that the application of CPR components enhances, and does not interfere with the existing mechanical activity of the heart. The device may also potentially be used in patients suffering severe shock with residual signs of life.

Figure 4:
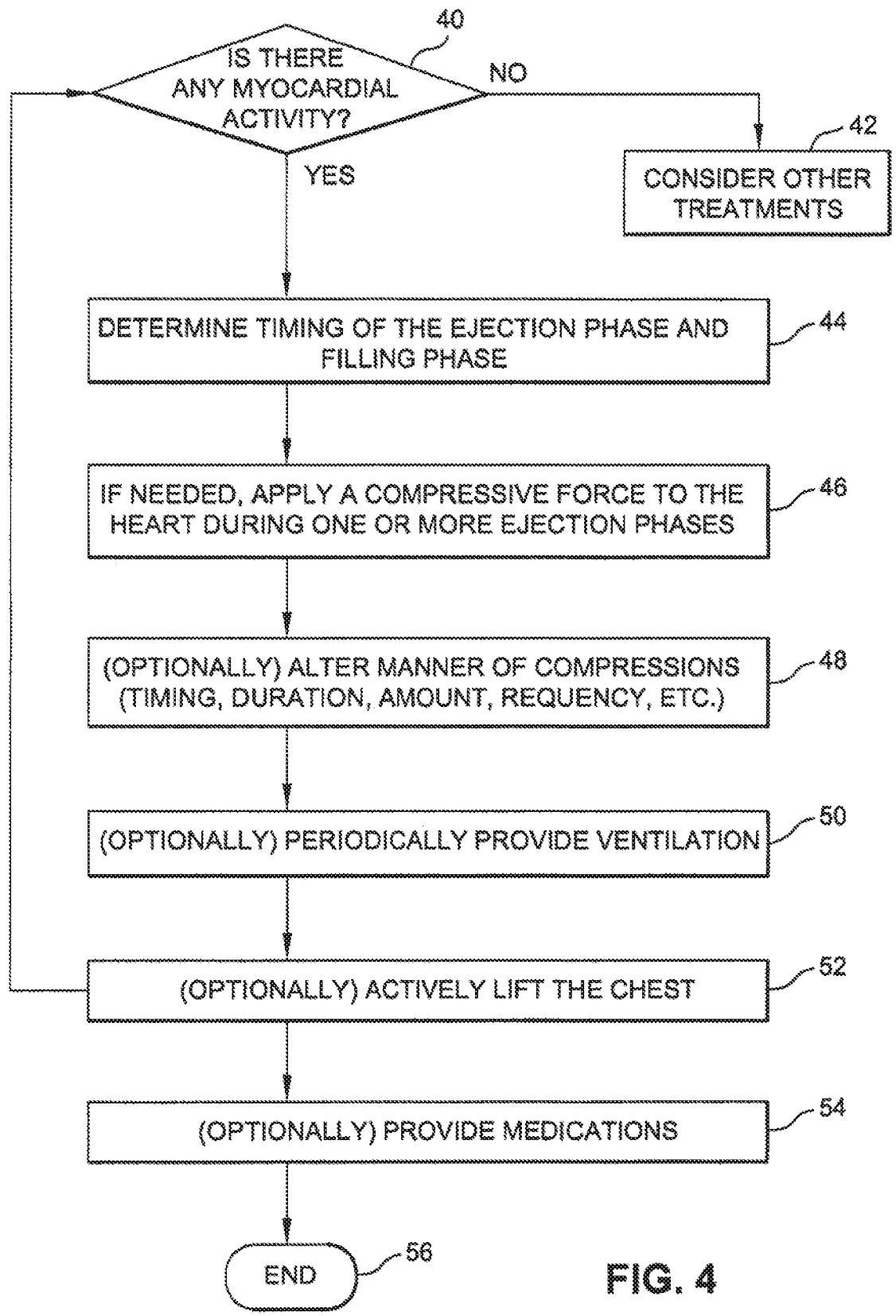
FIG. 4 is a flow chart illustrating one method for improving the cardiac output of a patient according to the invention.

Referring to FIG. 4, one exemplary method for treating a patient suffering from ailments ranging from shock to PEA will be described. Initially, the patient is evaluated to determine if there is any myocardial activity as illustrated in step 40. If myocardial activity is not present, the rescuer may wish to consider other treatments as illustrated in step 42. For example, such treatments could include the use of a defibrillating shock as is known in the art. If some myocardial wall activity is detected, the process proceeds to step 44 where the timing of the ejection phase and filling phase is determined. As previously described, this may be determined by the use of a sensor that is used to sense myocardial wall activity. Also determined may be the vector and baseline oxygen or energy state of vital organs. Depending on the amount of activity exhibited by the heart, a compressive force or another phasic therapy may be applied to the heart during one or more of the ejection phases as illustrated in step 46. This may be accomplished by using automated equipment or by using manual techniques. In either event, the applied compressive forces may be synchronized with the ejection phase so that the compressive forces do not interfere with the refilling phase. Optionally, as illustrated in step 48, the manner of compressions may be varied. This may include the time, duration, amount, frequency, vector, and the like. These variables may be initially set after measuring the amount of myocardial wall activity and may be changed or varied throughout the procedure depending on the patient's physiological condition.

As illustrated in step 50, the patient may periodically be provided with ventilations. The phases of ventilations may also be synchronized with the sensed ejection phases and refilling phases as measured in step 44. Further, the ventilations may be coordinated with the application of the chest compressions.

In some cases, the patient's chest may be actively lifted in an alternating manner with chest compressions as illustrated in step 52. In such cases, the chest may be lifted during the filling phase as measured in step 44.

As another optional step 54, the patient may periodically be provided with medications as part of the treatment. Examples of medications that may be applied include epinephrine, vasopressin, amiodarone, and the like. Alternative phasic therapies for use in step 46 may also be synchronized with residual myocardial activity. These other phasic therapies may include, among others: abdominal counterpulsation, ventilation, phasic limb-compression, myocardial electrical stimulation, intravascular fluid shifting, intravascular balloon inflation-deflation, application of transthoracic electromagnetic irradiation.

Throughout the procedure, the patient's heart may be continually monitored to determine myocardial activity as well as other physiological conditions. For example, after each of the treatments in steps 46, 48, 50, 52 and 54, the condition and response of the patient is monitored. Depending on the sensed response and condition, the selection and application of these treatments may be adjusted to achieve a desired response and condition of the patient. Depending on the patient's condition, any of the items discussed in steps 44-54 may be varied or stopped over time. At step 56, the process ends.

Figure 5:
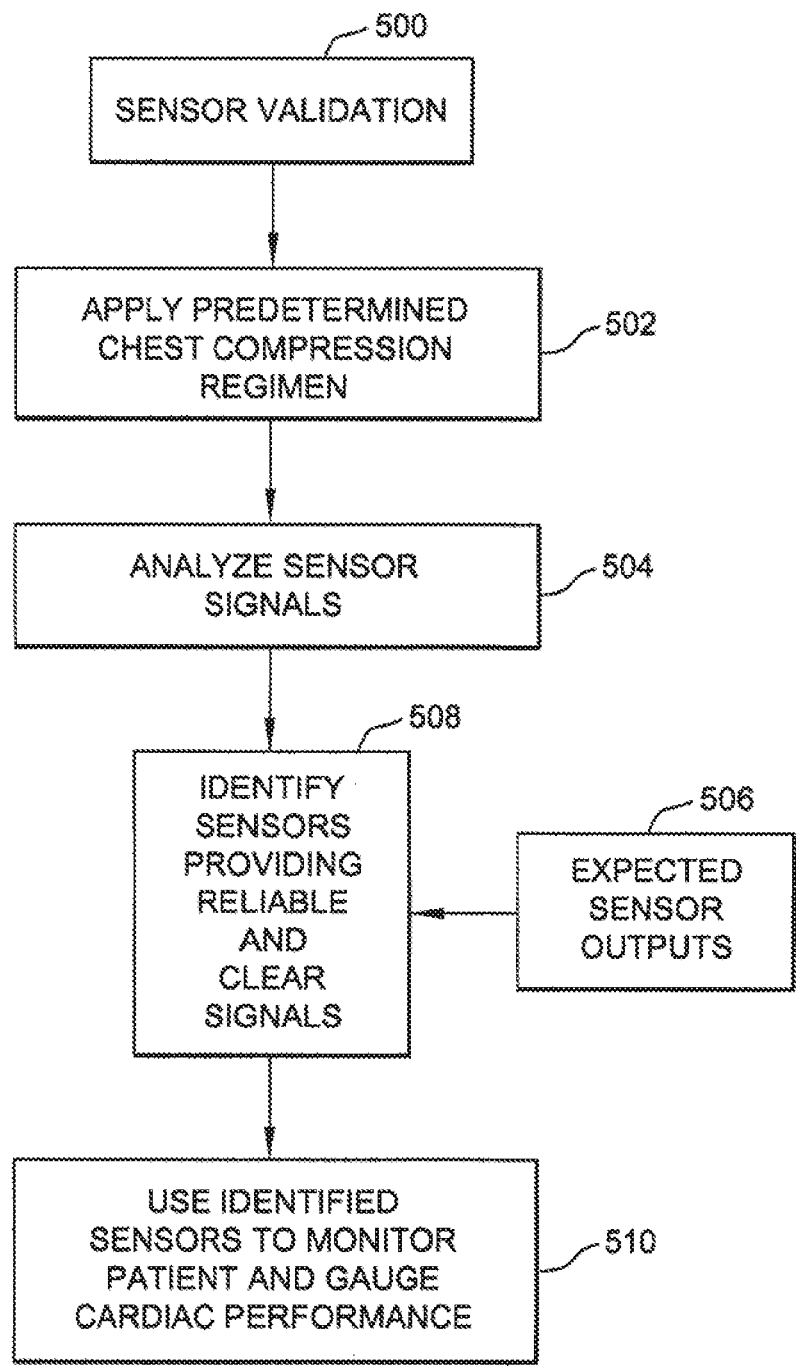
FIG. 5 is a flow chart illustrating a method to validate sensors used to detect myocardial motion and other patient parameters.

FIG. 5 is a flow chart illustrating an exemplary process executed by the controller 14 to validate the sensors 12 shown in FIG. 1. The sensor validation process 500 may be embodied in an algorithm stored as software or firmware in electronic memory of the controller 14 and executed by a processor of the controller. The sensor validation process 500 may include applying a predetermined regimen 502 chest compression regimen, such as a regimen of one or more chest compressions of predetermined force(s), vector(s), frequency and location(s) on the chest. Each of the sensors generate and output signals to the controller that indicate a condition of the patient being sensed by each of the sensors.

The controller analyzes 504 the output signals to determine which of the output signals or group of signals best indicate the condition of the patient, such as cardiac output.

The algorithm 500 may compare the actual output signals to expected sensor output signals 506 stored in the memory of the controller. Based on the comparison, the controller identifies 508 the sensor(s) generating signal(s) that accurately and clearly report the condition of the patient in response to the regimen of chest compression(s).

The sensors identified in step 510 are deemed to be best suited to sense myocardial activity may depend on the particular patient and the circumstances of the PEA condition. The sensor validation procedure 500 may be performed at the initiation of chest compressions and periodically thereafter, especially if myocardial output does not improve in an expected manner.

Once the sensors have been validated, signals generated by the sensors identified in the validation process are used to provide feedback to the algorithms, such as shown in FIGS. 4 and 6, that determine the chest compressions and optionally synchronized ventilation and synchronized electrical stimulation of the heart. Using these signals, the algorithms may generate and adjust a regimen for chest compressions and ventilations of the patients. The regimen may dictate the force to be applied by the chest compressions, the frequency of the chest compressions, the shape and duration of the force applied by the chest compressions, the synchronization and phasing of the chest compressions with sensed myocardial activity, the location on the chest or other body location, e.g., legs, of compressions, and a vector of the chest or other compressions. The algorithms may vary the regimen to optimize a condition of the patient, such as to increase sensed actual cardiac output or actual hemodynamics, e.g., pulsatile blood flow.

Figure 6A:
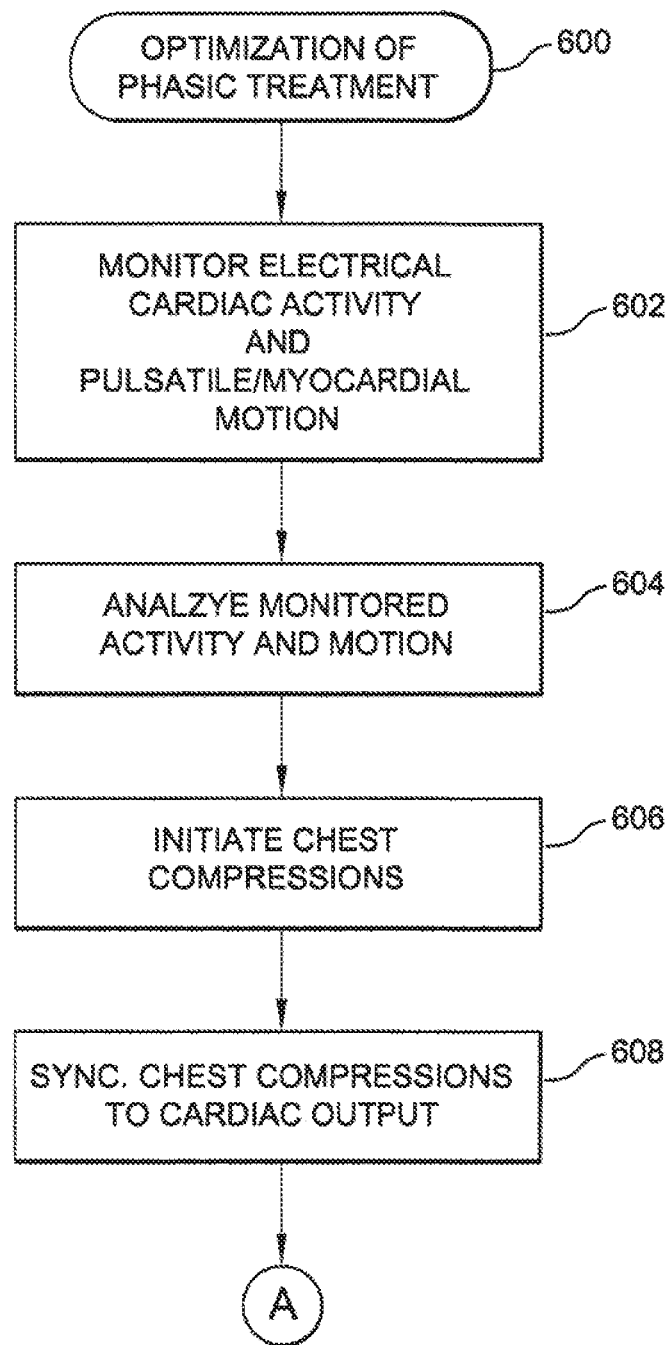
FIGS. 6A and 6B are a flow chart of an exemplary algorithm to determine when to initiate chest compressions and optimize a chest compression regimen that may be combined with ventilation of the patient and electrical stimulation of the heart.
Figure 6B:
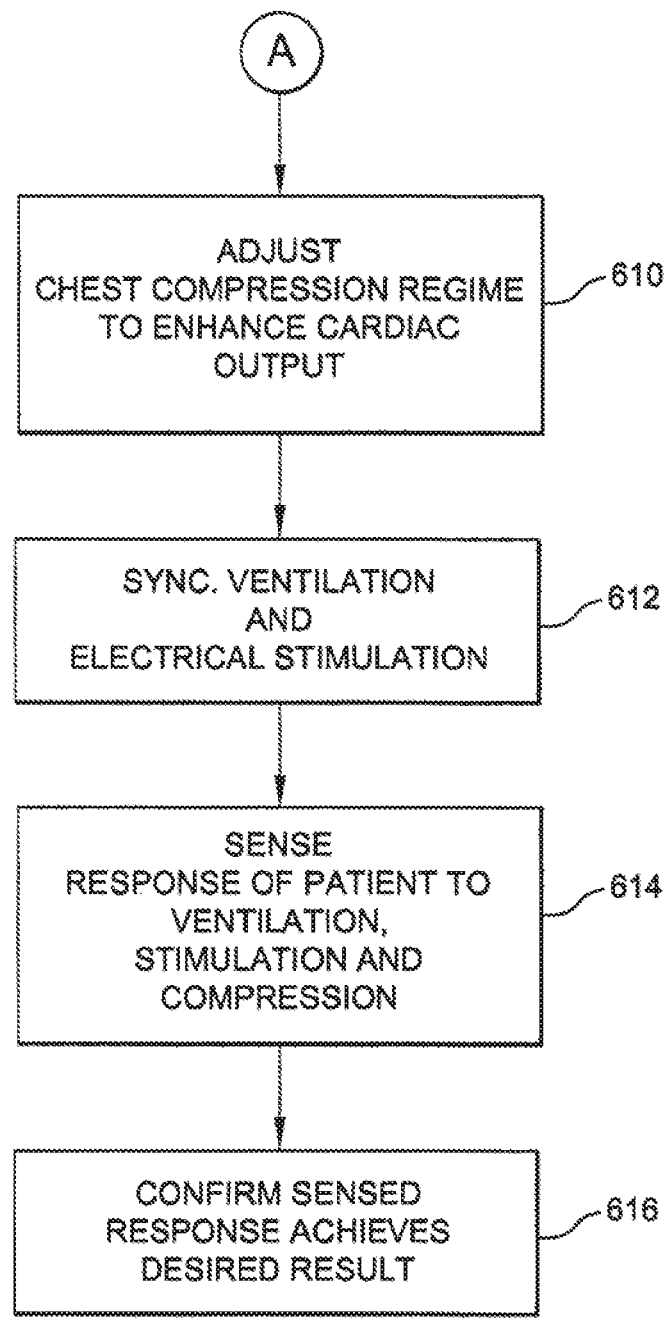

FIGS. 6A and 6B are a flow chart of an exemplary algorithm 600 to determine when to initiate chest compressions, synchronize the chest compressions to cardiac activity and optimize the chest compression regimen which may be combined with ventilation of the patient and external electrical stimulation of the heart. In step 602, sensors applied to a patient suffering from shock or other cardiac aliment are monitored to detect cardiac electrical activity, e.g., electrocardiography (ECG/EKG), and to detect directly myocardial motion or pulsatile blood flow.

The sensor signals from step 602 provide the controller and the health care provider with information from which to determine whether to initiate chest compressions. For example, if the ECG signals indicate a steady, regular heart beat, the controller may determine that chest compressions are not needed, in steps 604 and 606. The signals from step 602 may be analyzed in step 604 to determine whether, for example, the ECG signals do not indicate a regular or sufficiently frequent heart beat. If the ECG signals indicate an irregular or infrequent heart beat, the controller may determine (604) that chest compressions are needed (606) to augment the remaining natural cardiac activity.

In addition, signals from the sensors detecting pulsatile blood flow and actual myocardial motion may be compared to the signals of cardiac electrical activity to confirm that the cardiac electrical activity is synchronized with actual cardiac output. If the there is no detectable cardiac electrical activity or if the cardiac electrical activity is disassociated with pulsatile or actual ejection of blood from the heart, the controller may rely on sensors detecting actual myocardial movement or pulsatile blood flow to monitor cardiac movement and output. The controller may perform a sensor validation algorithm (FIG. 5) to identify the sensors generating signals that accurately and clearly indicate cardiac movement and output.

After chest compressions have been initiated (step 606), the controller executes algorithms (FIG. 4) to synchronize (step 608) the chest compressions to the sensed myocardial motion, e.g., to an EKG/ECG signal or to sensor signals indicative of pulsatile or actual myocardial motion. While the chest compressions are applied, the controller relies on the validated sensors to provide feedback information regarding the contraction or ejection phase of the heart and the cardiac output of the heart.

In step 610, the controller executes algorithms (see FIG. 4) to optimize the chest compression regimen to enhance cardiac output. The chest compression regimen may be optimized using the signals generated by the validated sensors that provide information regarding cardiac output or another condition of the patient. The chest compression regimen may be optimized by varying the parameters of the chest compressions, such as varying the force and frequency of the compressions, the location of the compressions on the chest or other location on the patient and the phase of the synchronization between the compressions and the contraction/ejection of the heart. To optimize, the controller may vary one or more of the parameters of the chest compressions and analyze the response to the varied parameter(s) generated by the validated sensors.

Examples of parameters of the chest compression that may be varied and optimized include: the depth of the compressions made into the chest; the during of each compression, the velocity of each compression, the force applied to the chest during each compression, the rate of the chest compression, the shape of the compression (such as the duration at the depth of the compression), the location of the compression on the chest, and the phase of synchronization between the chest compression and the sensed cardiac activity. While varying one or more of these parameters, the response of the patient to the chest compression is monitor and a determination is made at to which combination of parameter setting yields the most advantageous response, such as strongest arterial pulse flow.

In step 612, the controller synchronizes ventilation of the patient and electrical stimulation of the heart to the chest compressions or to contraction/ejection of the heart. The electrical stimulation may be repeated and coordinated with the chest compressions. In step 614, the sensors, e.g., validated sensors, detect or measure the response of the patient to one or more of the compressions, ventilation and electrical stimulations. In step 616, a determination is made that the detected or measured response is achieving a desired result or outcome in the patient. If a desired result or outcome is not being achieved, the controller may adjust the compressions, ventilation or electrical stimulations until the desired result or outcome is achieved.

Figure 7A:
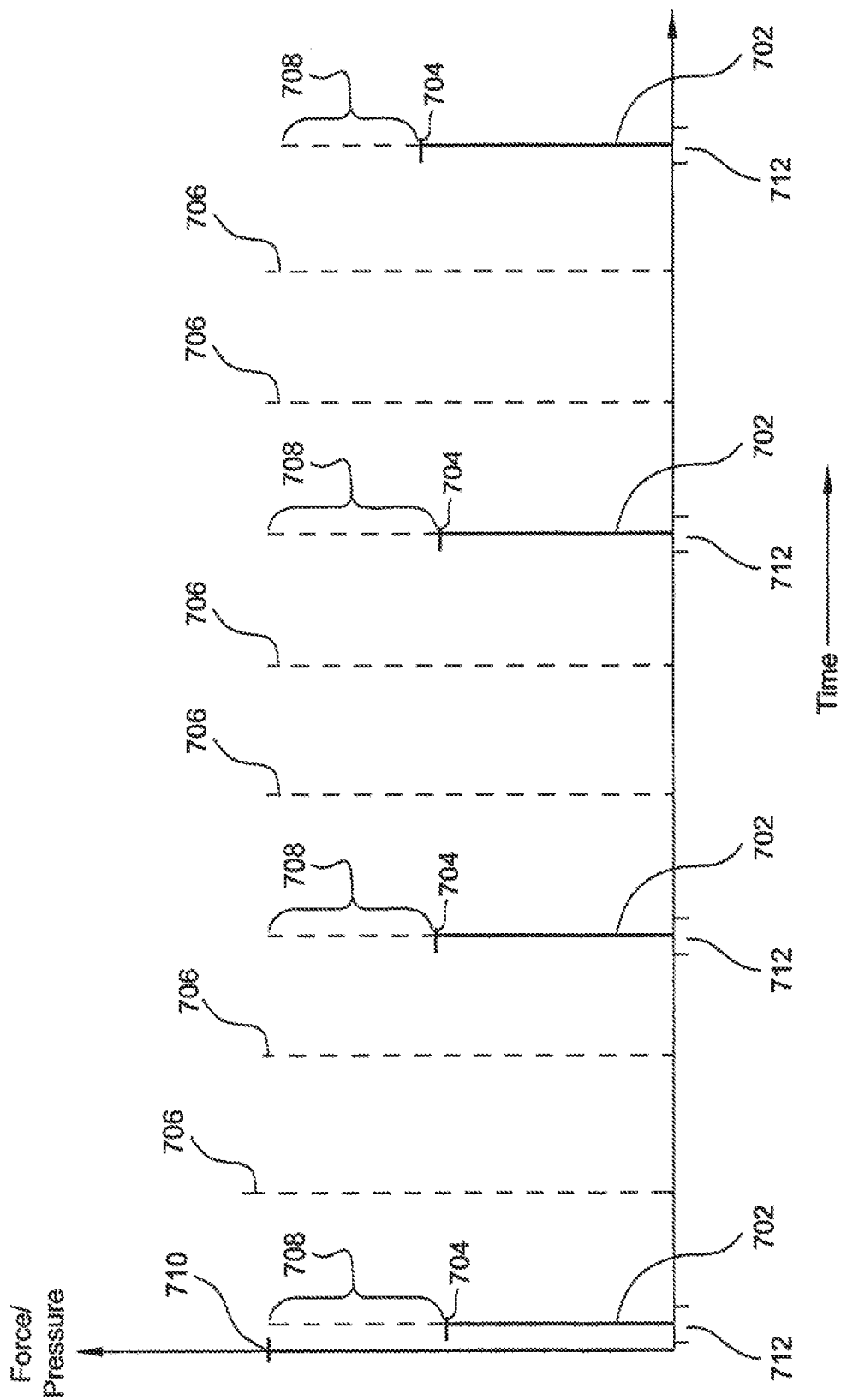
FIG. 7A is a chart illustrating chest compressions of varying force applied in synchronization with a slow heart beat.

FIG. 7A is a chart 700 illustrating chest compressions applied in synchronization with a slow heart beat. Patients suffering a cardiac arrhythmia may have a slow heartbeat 702, e.g., a heartbeat below 55 to 60 beats per minute. The controller detects the heart beat from sensor signals indicating pulsatile flow and determines that the heart beat is slow and sensors detecting aortic pressure that provide signals indicating a weak heartbeat. To compensate for a slow or weak heartbeat, the controller generates commands 706, 708 to actuate a chest compression device or audible and visible commands to notify when chest compressions are to be applied and, optionally, to indicate a force to be applied by the chest compressions.

The audible commands may include computer generated voice commands such as, during the chest compressions, "press softer", "press harder", "press deeper", "press shallower", "press faster (or slower)" and "press lower (or higher) on the abdomen". Similarly, visible commands may be computer generated display images corresponding to these voice commands. The audible and visible commands may be the result of computer analysis of feedback signals generated from sensors monitoring the pulsatile flow, myocardial activity, breathing or other condition of the patient.

The force of the chest compressions to be applied is indicated by the length of the dotted line 706, 708 shown in FIG. 7. The chest compressions 708 that coincide with each heartbeat 704 may be synchronized with the ejection phase of the heartbeat. Chest compressions may not be applied during the ejection phase and during the period during which the heart is susceptible to comodio cordius. Additional chest compressions 706 are applied during periods between the natural heart beat. The force of these chest compressions 706 may be sufficient to result in a cardiac output which approximates the desired cardiac output 710. The level of force of the chest compressions that is commanded by the controller may be varied based on feedback signals from sensors detecting the cardiac output. Further the chest compressions 708 that coincide with the heartbeat may be applied at a substantially lower force than the chest compressions 706 that are out-of-phase with the natural heartbeat. The lower force of the chest compressions 706 are intended to augment the natural contraction of the heart to ejection blood at a sufficient force to achieve a desired level of cardiac output. The controller estimates the lower level of force to be applied by the chest compressions 708 (as indicated by the short dotted lines associated with 708 on FIG. 8) and issues commands to the chest compression device to apply a certain level of chest compressions. The controller may also issue an alert to a health care provider to not apply a force to the chest during a period 712 coinciding with the heartbeat to avoid having chest compressions applied which counter act the natural heartbeat 704.

Figure 7B:
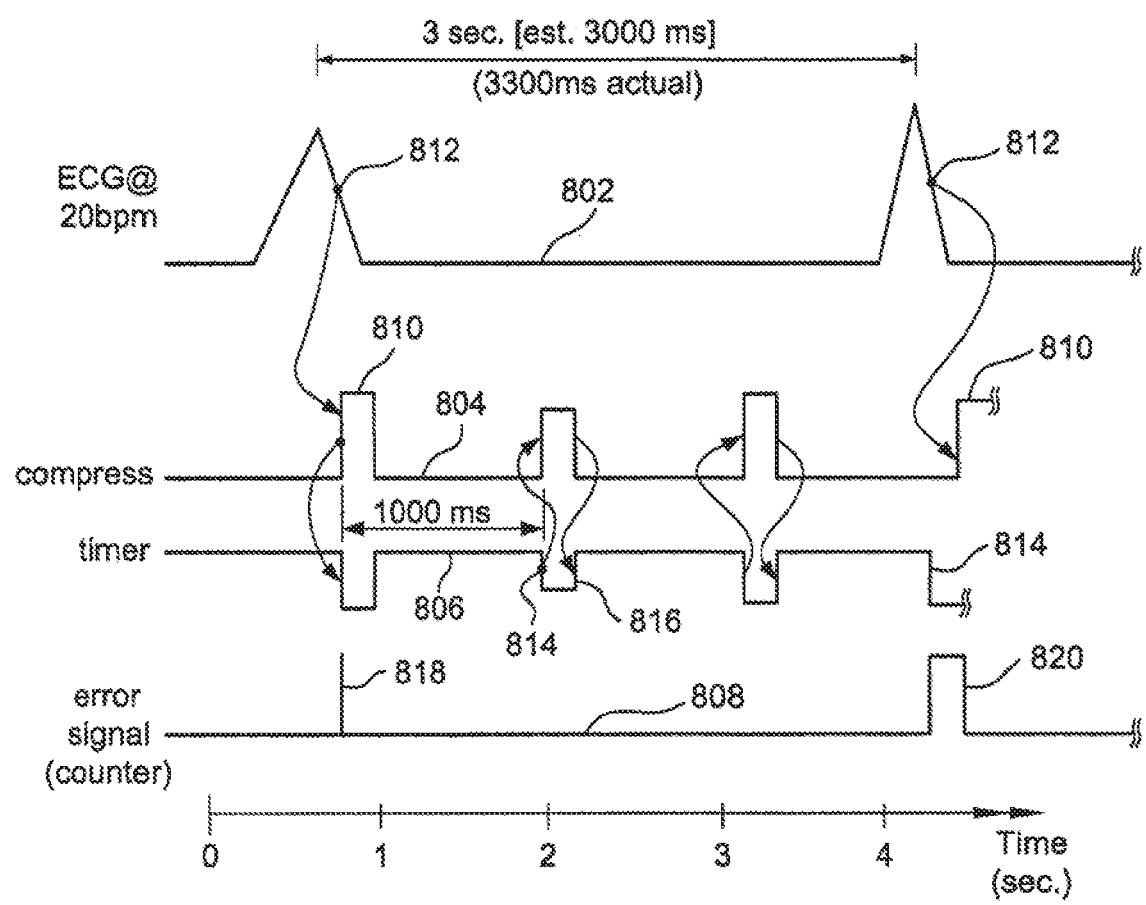
FIG. 7B is a chart illustrating a method to correct a synchronization error between chest compressions and a heart beat.

FIG. 7B is a time line chart including a line 802 indicating a slow heart beat, a line 804 indicating chest compressions occurring more frequently than the heart beat, a line 806 indicating a timer triggering the chest compression, and a line 808 indicating an error correction counter. As indicated by line 802, the heartbeat is naturally occurring once every three (3) seconds, in this example. This slow heart beat may be detected by its ECG electrical signal. Because the heartbeat is slow, chest compressions (see line 804) are applied more frequently, e.g., every second, than the heart beat. The higher frequency of the chest compressions may be a harmonic of the frequency of the heart beat. A harmonic frequency should maintain synchronization between the chest compressions and the natural heart beat.

The chest compressions are synchronized with the heart beat. In this example, every third chest compression 810 coincides with the heart beat. It is desirable that the chest compression be synchronized with the ejection phase of the heartbeat. For example, the start of the chest compression should coincide with the QRS electrical signals 812 that precedes the ejection phase of the cardiac cycle.

A timer in the system that controls or triggers the chest compressions generates a timing signal 806 that triggers the start 814 and end 816 of each chest compression. The timing signal 806 triggers chest compressions at regular intervals, such as about every second. The regular intervals of the chest compressions may, over time, become unsynchronized with the heart beat 802.

To maintain synchronization between the chest compressions and the heart beat, a timer or counter generates an error signal 808. The timer is in the system that controls or triggers the chest compressions. The error signal is used to measure the period between the QRS signal 812 and the chest compression 810, e.g., the initiation of the chest compression, nearest the QRS signal. If the QRS signal 812 and the chest compression are synchronized, an error period 818 may be instantaneous or brief as shown by the error signal 808. A longer error signal 820 results if the initiation of the chest compression does not occur at about the same time as the QRS signal. As an alternative to the QRS signal, the error period 818, 820 may be determined based on sensed pulsatile flow or sensed mechanical myocardial activity.

The error period is triggered by the chest compression timing signal 806 and particularly by the signal 814 initiating the chest compression. The error period 820 may be a positive period if the chest compression starts 814 before the QRS period. A positive error period is applied by the system to delay the next chest compression by the duration of the period. The delay should cause the chest compression that coincides with the next heart beat to by synchronized with that heart beat. Similarly, the error period 820 may be a negative period if the QRS signal precedes the chest compression signal. A negative error period 820 may be applied to advance the occurrence of the next chest compression by the duration of the negative error period. The advance should cause the chest compression that coincides with the next heart beat to be synchronized with the heart beat.

The determination of the error period is similar to a phase lock loop control technique conventionally used in control systems. The delay or advance due to an error period 820 to the chest compression signal 814 may occur entirely in a period between two chest compressions, or may be distributed evenly between two or more periods depending on the length of the delay or advance. Similarly, the error period 820 may not result in a delay or advance if the period is shorter than a threshold duration, e.g., 10 milliseconds.

Figure 8:
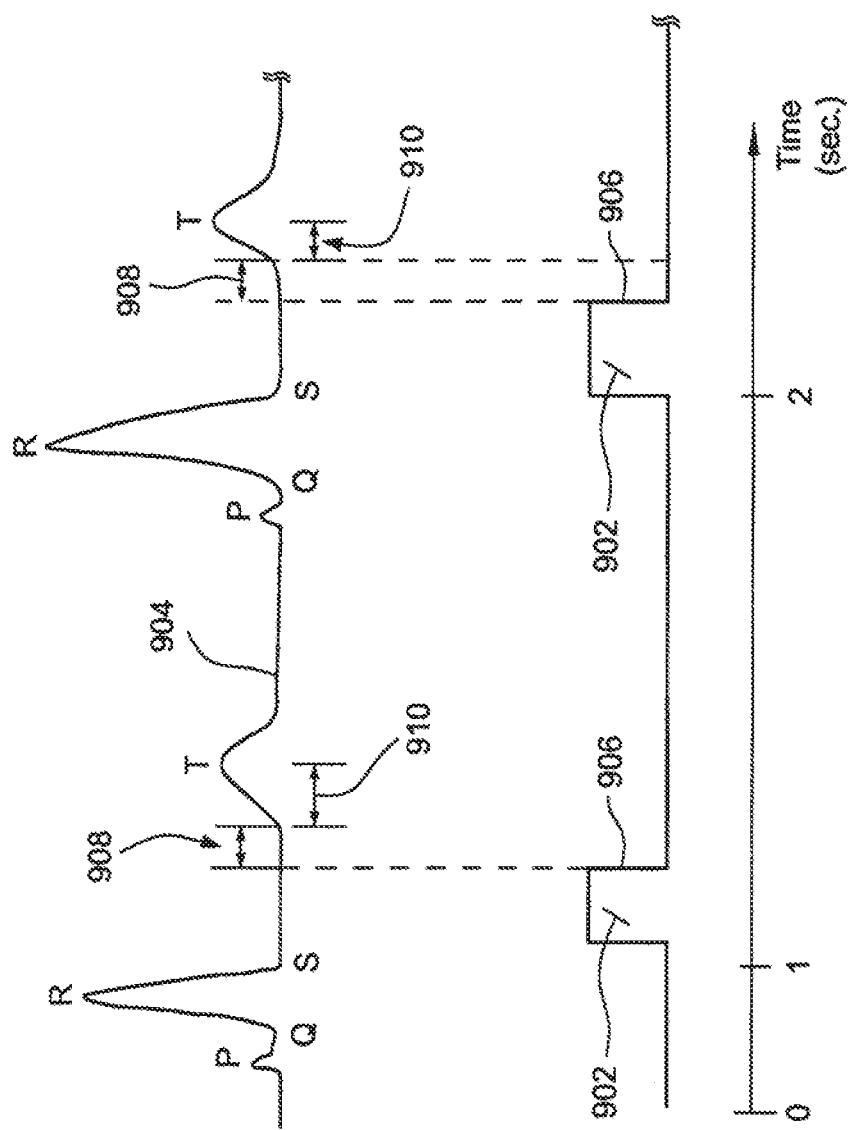
FIG. 8 is a chart illustrating a method to synchronize a chest compression to a heart beat.

FIG. 8 is a chart illustrating a method to synchronize chest compressions 902 to a heart beat shown by line 904. The electrical signals of a heart beat conventionally include a P-wave, the QRS waves, and the T wave. It is well known that the P-wave indicates atrial electrical activation (depolarization), the QRS wave complex indicates a rapid depolarization of the ventricles and the start of the cardiac ejection phase, and the T wave indicates the recovery (repolarization) of the ventricles. The chest compression 902 optimally occurs during the ejection phase immediately following the QRS wave.

The chest compression is terminated 906 before a safety period 908 before the T wave. The period may be a short duration such as 10 to 200 milliseconds. The safety period 908 is applied to ensure that the chest compression does not continue to the T wave particularly during the portion 910 of the T wave during which the heart is vulnerable to commotio cordis, which is a disruption of the heart rhythm due to a blow to the heart during the T wave.

Figure 9:
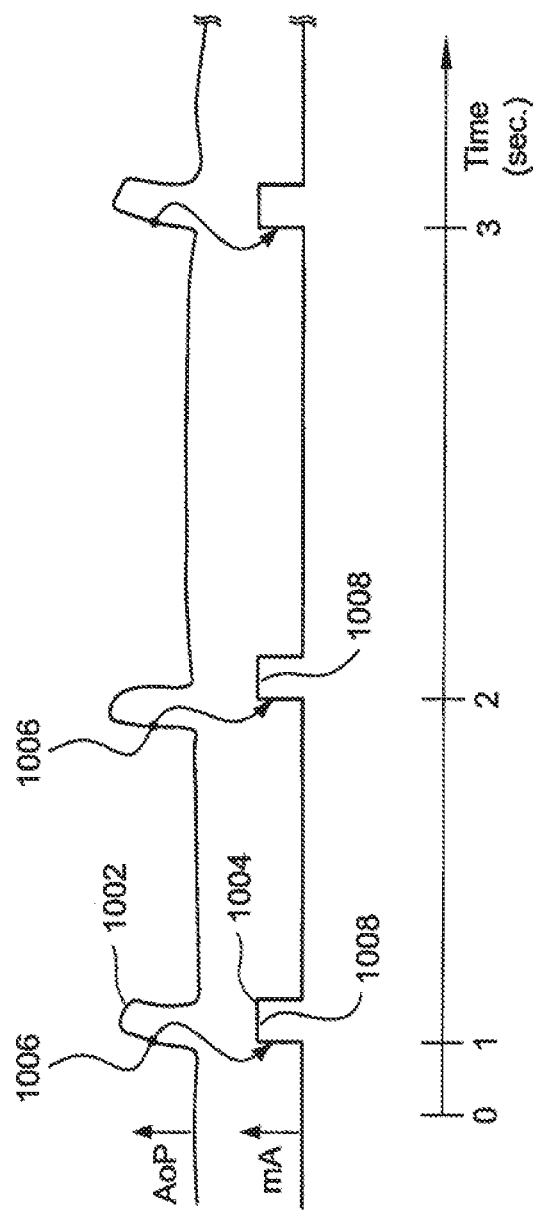
FIG. 9 is a chart illustrating a method to synchronize electrical cardiac stimulation to pulsatile flow or mechanical myocardial activity.

FIG. 9 is a chart illustrating a method to synchronize electrical cardiac stimulation 1002 to aortic pressure (AoP) pulses 1004 due to myocardial mechanical activity. The aortic pressure (AoP) pulses may be detected based on ECG signals, pulsatile flow and myocardial activity. If the heart is producing ECG signals that are synchronized with the myocardial mechanical activity, the QRS signal 1006 of the ECG may be applied to trigger each electrical cardiac stimulation pulse 1008. Alternatively, the electrical stimulation pulses 1008 may be trigger based on pulsatile flow or sensed myocardial mechanical activity.

The electrical stimulation pulses 1008 may be applied at a frequency greater than the natural heat beat, such as in the manner shown and described in connection with FIG. 7B. Further, the frequency and timing of the electrical stimulation pulses may be adjusted in the manner shown and described in connection with FIG. 8.

The electrical pulse signals 1008 may be applied to the chest of the patient or directly to the heart for each heart beat. The electrical signal is applied for each heart beat to assist the heart in restoring natural electrical stimulation, to resynchronize the natural electrical stimulation to the myocardial mechanical activity or to supplement the natural electrical stimulation to increase the ejection force from the myocardial mechanical activity.

The electrical pulse signals may be a "pacer pulse" such as that delivered by a conventional pacemaker and having a value of less than 500 milliamps (mA). Alternatively, the electrical pulse signals may shock the heart by delivering a pulse of between 500 mA to 5 A, which is similar to a low energy defibrillator pulse.

The application of the electrical pulse signals for each heart beat is in contrast to a conventional pacemaker device that does not issue an electrical stimulation for each heart beat. A conventional pacemaker issues an electrical stimulation one if and when a timer expires without the occurrence of a natural heart beat. A conventional pacemaker issues an electrical signal when a natural heartbeat does not occur in a prescribed period and does not issue an electrical signal that is synchronized with a naturally heartbeat.

The invention has now been described in detail for purposes of clarity and understanding. However, it will be appreciated that certain changes and modifications may be practiced within the scope of the appended claims.

What is claimed is:

1. A system for improving cardiac output of a patient suffering from pulseless electrical activity, the system comprising
    at least one sensor configured to monitor myocardial activity of the patient and generate signals indicative of the myocardial activity;
    an automated chest compressor configured to apply chest compressions to the chest of the patient; and
    a controller communicatively coupled with the at least one sensor and the automated chest compressor, the controller configured to:
        receive the signals indicative of the myocardial activity from the at least one sensor,
        analyze the received signals to determine if the patient is suffering from pulseless electrical activity,
        determine a pattern of myocardial motion of the patient based on the received signals, and
        trigger the automated chest compressor to synchronize the applied chest compressions from the automated chest compressor with the pattern of myocardial motion of the patient.

2. The system of claim 1, wherein the at least one sensor is a plurality of sensors, and at least one of the plurality of sensors is configured to monitor pulsatile blood flow within the patient.

3. The system of claim 2, wherein the at least one sensor comprises one or more of electrocardiography sensors, Doppler ultrasonography sensors, plethysmography sensors, phonocardiography sensors, echocardiography sensors, and Transthoracic impedance sensors.

4. The system of claim 2, wherein the controller is configured to combine inputs from the plurality of sensors to increase sensitivity and specificity when detecting the myocardial activity or pulsatile blood flow of the patient.

5. The system of claim 2, wherein at least one of the plurality of sensors is configured to measure end-tidal carbon dioxide or aortic flow of the patient.

6. The system of claim 2, wherein the plurality of sensors includes an array of sensors applied to the body of the patient.

7. The system of claim 1, wherein the controller is configured to analyze the received signals to identify an ejection phase, a relaxation phase, and a filling of phase of a cardiac cycle of the patient.

8. The system of claim 7, wherein the controller is configured to trigger the automated chest compressor to apply the chest compressions to the chest of the patient, wherein the applied chest compressions are synchronized to a portion of the ejection phase of the cardiac cycle of the patient.

9. The system of claim 8, wherein the automated chest compressor includes an active chest decompression device that lifts the chest of the patient during the chest compressions.

10. The system of claim 9, wherein the controller is configured to trigger the automated chest compressor to synchronize the lifting of the chest of the patient with a portion of the relaxation phase.

11. The system of claim 8, wherein the controller is configured to transmit a command to the automated chest compressor to terminate the chest compression of the automated chest compressor immediately prior to a start of a T-wave.

12. The system of claim 7, further comprising a ventilator that is communicatively coupled to the controller and configured to be synchronized with the ejection phase and filling phase by the controller.

13. The system of claim 1, wherein the pattern of myocardial motion includes a natural heartbeat of the patient.

14. The system of claim 13, wherein the controller is further configured to transmit at least one trigger to the automated chest compressor more frequently than the natural heartbeat of the patient to cause the automated chest compressor to provide at least one chest compression to the patient between the natural heartbeat of the patient.

15. The system of claim 1, wherein the automated chest compressor includes a piston that provides chest compressions against the chest of the patient in a repeating manner.

16. The system of claim 1, wherein the automated chest compressor includes an inflatable vest that selectively inflates and deflates chambers within the inflatable vest to provide chest compressions to the chest and/or back of the patient.

17. The system of claim 1, wherein the controller further comprises a timer that is configured to generate a chest compression timing signal that provides an indication of when to trigger the automated chest compressor to provide the chest compression to the patient.

18. The system of claim 17, wherein controller is configured to determine an error period, the error period being a measure of time between a QRS signal of the patient and the chest compression provided by the automated chest compressor.

19. The system of claim 18, wherein the controller is configured to determine if the error period is positive, which indicates that the automated chest compressor initiated a chest compression before the measured QRS signal of the patient.

20. The system of claim 19, wherein the controller is configured to determine if the error period is negative, which indicates that the automated chest compressor initiated a chest compression after the measured QRS signal.

21. The system of claim 20, wherein the controller is configured to advance or delay the trigger of the chest compressions based on the error period in order to synchronize the chest compressions from the automated chest compressor with the QRS signal of the patient.

* * * * *

UNITED STATES PATENT AND TRADEMARK OFFICE
CERTIFICATE OF CORRECTION

PATENT NO. : 10,555,870 B2  
APPLICATION NO. : 15/791937  
DATED : February 11, 2020  
INVENTOR(S) : Norman A. Paradis et al.

Page 1 of 1

It is certified that error appears in the above-identified patent and that said Letters Patent is hereby corrected as shown below:

On the Title Page

On Page 2
Column 2 (Other Publications), Line 9, delete "Dissciation", insert -- Dissociation --
Column 2 (Other Publications), Line 12, delete ""Optomizlng", insert -- "Optimizing --
Column 2 (Other Publications), Line 15, delete "lntensivmed", insert -- Intensivmed --
Column 2 (Other Publications), Line 16, delete "Schmerztyer.", insert -- Schmertzler. --
Column 2 (Other Publications), Line 42, delete "cardipulmonary", insert -- cardiopulmonary --
Column 2 (Other Publications), Line 44, delete "Anaesthesist,", insert -- Anaesthetist --
Column 2 (Other Publications), Line 62, delete "aortomyop!asty", insert -- aortomyoplasty --

On Page 3
Column 2 (Other Publications), Line 13, delete "Anesthesiologh", insert -- Anesthesiology --
Column 2 (Other Publications), Line 16, delete "theraphy", insert -- therapy --
Column 2 (Other Publications), Line 17, delete "K!in", insert -- Klin --

In the Specification

Column 5, Line 20, delete "and or", insert -- and/or --
Column 6, Line 48, delete "oxymetry,", insert -- oximetry, --
Column 12, Line 20, delete "and or", insert -- and/or --

Signed and Sealed this  
Thirty-first Day of March, 2020

Andrei Iancu  
*Director of the United States Patent and Trademark Office*